United States Patent
Wang et al.

(10) Patent No.: US 12,385,046 B2
(45) Date of Patent: Aug. 12, 2025

(54) BAICALEIN- AND SCUTELLAREIN-SYNTHESIZING MICROORGANISM, PREPARATION METHOD AND APPLICATIONS THEREOF

(71) Applicant: CAS CENTER FOR EXCELLENCE IN MOLECULAR PLANT SCIENCES, Shanghai (CN)

(72) Inventors: Yong Wang, Shanghai (CN); Jianhua Li, Shanghai (CN); Chenfei Tian, Shanghai (CN)

(73) Assignee: CAS CENTER FOR EXCELLENCE IN MOLECULAR PLANT SCIENCES, Shanghai (CN)

( * ) Notice: Subject to any disclaimer, the term of this patent is extended or adjusted under 35 U.S.C. 154(b) by 1119 days.

(21) Appl. No.: 17/274,377

(22) PCT Filed: Sep. 6, 2019

(86) PCT No.: PCT/CN2019/104658
§ 371 (c)(1),
(2) Date: Mar. 8, 2021

(87) PCT Pub. No.: WO2020/048523
PCT Pub. Date: Mar. 12, 2020

(65) Prior Publication Data
US 2022/0033827 A1 Feb. 3, 2022

(30) Foreign Application Priority Data
Sep. 7, 2018 (CN) .......................... 201811043657.0

(51) Int. Cl.
*C12N 15/52* (2006.01)
*C07K 14/415* (2006.01)
*C12N 9/02* (2006.01)
*C12P 17/06* (2006.01)

(52) U.S. Cl.
CPC ............ *C12N 15/52* (2013.01); *C07K 14/415* (2013.01); *C12N 9/0042* (2013.01); *C12N 9/0071* (2013.01); *C12N 9/0073* (2013.01); *C12P 17/06* (2013.01); *C12Y 106/02004* (2013.01); *C12Y 114/14* (2013.01)

(58) Field of Classification Search
CPC .... C12N 15/52; C12N 9/0042; C12N 9/0071; C12N 15/70; C12N 15/75; C12N 15/81; C07K 14/415; C07K 2319/24; C07K 2319/10; C07K 2319/20; C07K 2319/00; C12P 17/06; C12Y 106/02004; C12Y 114/14; C12Y 114/14001; Y02A 50/30
See application file for complete search history.

(56) References Cited

FOREIGN PATENT DOCUMENTS

CN 106318920 A * 1/2017 .......... C12N 9/0071

OTHER PUBLICATIONS

Leonard et al., "Functional expression of a P450 flavonoid hydroxylase for the biosynthesis of plant-specific hydroxylated flavonols in *Escherichia coli*." Metabolic engineering vol. 8,2: 172-81 (available online Dec. 2005); doi: 10.1016/j.ymben.2005.11.001 (Year: 2005).*
Zhu et al., "Efficient Synthesis of Eriodictyol from L-Tyrosine in *Escherichia coli*," Applied and Environmental Microbiology, Mar. 7, 2014, vol. 80, No. 10, pp. 3072-3080, (on IDS dated Nov. 15, 2022) (Year: 2014).*
Leonard et al. 2005. "Investigation of two distinct flavone synthases for plant-specific flavone biosynthesis in *Saccharomyces cerevisiae*". Applied and environmental microbiology, 71(12), 8241-8248. https://doi.org/10.1128/AEM.71.12.8241-8248.2005 (Year: 2005).*
Zhao et al. 2018. "Two CYP82D Enzymes Function as Flavone Hydroxylases in the Biosynthesis of Root-Specific 4'-Deoxyflavones in Scutellaria baicalensis". Mol. Plant. 11, 135-148 (Year: 2018).*
Morrone et al. 2010. "Characterization of the kaurene oxidase CYP701A3, a multifunctional cytochrome P450 from gibberellin biosynthesis." Biochemical Journal 431.3: 337-347 (11 pages total). https://doi.org/10.1042/BJ20100597 (Year: 2010).*
Zhu et al. 2014. "Efficient Synthesis of Eriodictyol from L-Tyrosine in *Escherichia coli*," Applied and Environmental Microbiology, Mar. 7, 2014, vol. 80, No. 10, pp. 3072-3080 (Year: 2014).*
Biggs et al. 2016. "Overcoming heterologous protein interdependency to optimize P450-mediated Taxol precursor synthesis in *Escherichia coli*". Proc Natl Acad of Sci U.S.A. 113(12), 3209-3214. https://doi.org/10.1073/pnas.1515826113 (Year: 2016).*
Machine translation of the Description of CN106318920A (Tianjin Institute of Industrial Biotechnology, CAS, originally published on Jan. 11, 2017). Translation downloaded from EPO on Apr. 16, 2024. 33 pages total. (Year: 2017).*
Artigot et al., "Expression of Flavonoid 6-hydroxylase Candidate Genes in Normal and Mutant Soybean Genotypes for Glycitein Content," Molecular Biology Reports, May 22, 2013, vol. 40, No. 7, pp. 4361-4369.
Biggs et al., "Overcoming heterologous protein interdependency to optimize P450-mediated Taxol precursor synthesis in *Esherichia coli*," Proceedins of National Academy of Sciences of the United States of America, Mar. 22, 2016, vol. 113, No. 12, pp. 3209-3214.
Li et al., "Production of Plant-specific Flavones Baicalein and Scutellarein in an Engineered *E. coli* from Available Phenylalanine and Tyrosine," Metabolic Engineering, Nov. 26, 2018, vol. 52, pp. 124-133.
Mayer et al., "P450 Reductase 2 [*Arabidopsis thaliana*], Accession No. AEE85737.1," NCBI GenBank, Jul. 20, 2017.

(Continued)

Primary Examiner — Terry A McKelvey
Assistant Examiner — Andrew T Moehlman
(74) Attorney, Agent, or Firm — Greenberg Traurig, LLP; Melissa Hunter-Ensor

(57) ABSTRACT

Provided are a baicalein- and scutellarein-synthesizing microorganism, a preparation method for same, and applications thereof. By modifying a heterologous metabolic pathway of a host cell per a genetic engineering method, acquired is an engineered strain providing a high yield of baicalein and scutellarein. Also provided is a process for utilizing the engineered strain to produce baicalein and scutellarein.

7 Claims, 7 Drawing Sheets
Specification includes a Sequence Listing.

(56) References Cited

OTHER PUBLICATIONS

NCBI GenBank Accession No. AAA33883.1, Apr. 27, 1993.
NCBI GenBank Accession No. KF765780.1, Jul. 17, 2014.
NCBI GenBank Accession No. KF765781.1, Jul. 17, 2014.
NCBI GenBank Accession No. KF765782.1, Jul. 17, 2014.
NCBI GenBank Accession No. ASW21050.1, Sep. 5, 2017.
NCBI GenBank Accession No. NP_849472.2, Feb. 14, 2019.
NCBI UniProtKB/Swiss-Prot Accession No. Q7XZQ8.1, Dec. 2, 2020.
Pandey et al., "Microbial production of natural and non-natural flavonoids: Pathway engineering, directed evolution and systems/synthetic biology", Biotechnology Advances, 2016, vol. 34, pp. 634-662.
Uno et al., "Metabolism of 7-ethoxycoumarin, Safrole, Flavanone and Hydroxyflavanone by Cytochrome P450 2A6 Variants," Biopharmaceutics & Drug Disposition, Dec. 4, 2012, vol. 34, No. 2, pp. 87-97.
Uno et al., "Point Mutation of Cytochrome P450 2A6 (a Polymorphic Variant CYP2A6.25) Confers New Substrate Specificity Towards Flavonoids," Biopharmaceutics & Drug Disposition, Aug. 31, 2015, vol. 36, No. 8, pp. 552-563.
Zhao et al., "Scutellaria Baicalensis Cytochrome P450 CYP82D1.1 mRNA, Complete Cds; Chromoplast, Accession No. MF363006.1," NCBI GenBank, Sep. 5, 2017.
Zhao et al., "Two CYP82D Enzymes Function as Flavone Hydroxylases in the Biosynthesis of Root-Specific 4'-Deoxyflavones in Scutellaria Baicalensis," Molecular Plant, Jan. 31, 2018, vol. 11, No. 1, pp. 135-148.
Zhu et al., "Efficient Synthesis of Eriodictyol from L-Tyrosine in *Escherichia coli*," Applied and Environmental Microbiology, Mar. 7, 2014, vol. 80, No. 10, pp. 3072-3080.
International Search Report issued in corresponding International Patent Application No. PCT/CN2019/104658, mailed Dec. 2, 2019.

\* cited by examiner

Baicalein    Scutellarein

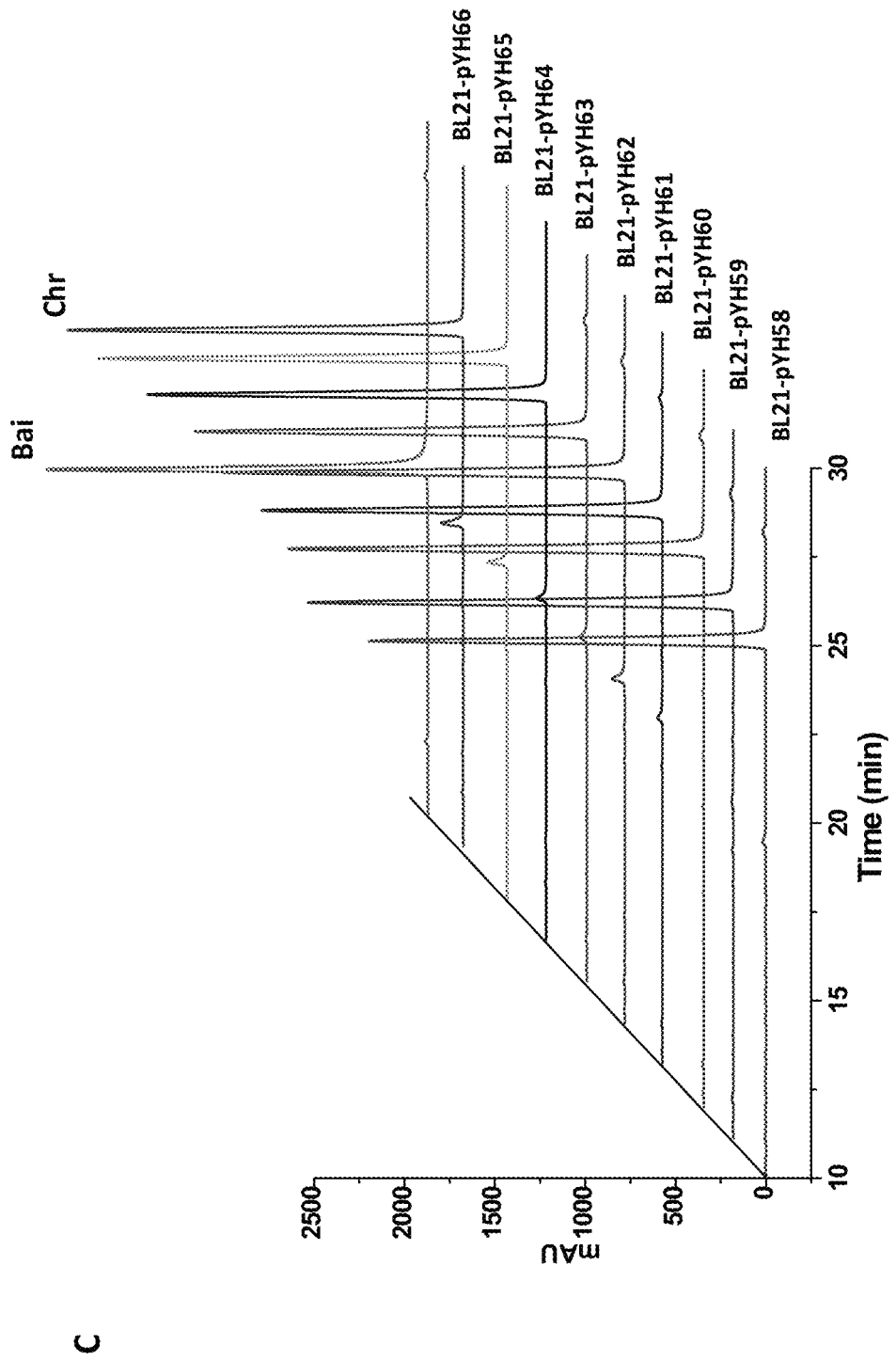
Figure 9, continued

BAICALEIN- AND SCUTELLAREIN-SYNTHESIZING MICROORGANISM, PREPARATION METHOD AND APPLICATIONS THEREOF

CROSS REFERENCE TO RELATED APPLICATIONS

This application is a U.S. National Phase application under 35 U.S.C. 371 of International Application No. PCT/CN2019/104658 filed Sep. 6, 2019, which claims priority to and the benefit of Chinese Patent Application No. 201811043657.0 filed Sep. 7, 2018, the entire disclosure of each of which is incorporated herein by reference.

FIELD

The invention relates to the technical fields of synthetic biology and medicine, in particular to a microorganism for synthesizing baicalein and scutellarein, a preparation method and application thereof.

BACKGROUND

*Scutellaria baicalensis* Georgi is a famous traditional medicine in China, which is a *Labiatae* plant. Traditional Chinese medicine (TCM) Radix Scutellariae is the dry root of *Scutellaria baicalensis* Georgi, which has a long medicinal history and can be used for the treatment of wind heat, damp heat and other diseases. Erigerontis Herba is the dry herb of *Erigeron breviscapus*. It is cold in nature and bitter in taste. It has the functions of anti-inflammatory and analgesic, promoting blood circulation and removing blood stasis, eliminating wind and dampness. Extract of *Scutellaria baicalensis* Georgi and *Erigeron breviscapus* have long been widely used in TCM preparations. The main raw materials of Yinhuang tablet, Shuanghuanglian oral liquid and Lanqin oral liquid are extract of *Scutellaria baicalensis* Georgi. The main active ingredient of Qingkailing is baicalein, which has the effect of anti-inflammatory, prevention and treatment of diarrhea, liver disease and tumor. The common dosage forms of *Erigeron breviscapus* include Breviscapine tablet and Breviscapine oral liquid, which can be converted to scutellarein and absorbed by an organism. Therefore, baicalein and scutellarein have a certain value in the development of new drugs.

Baicalein and scutellarein are two important flavonoids (flavones) with similar structures. The molecular formula of baicalein is $C_{15}H_{10}O_5$ with a molecular weight of 270.24, while molecular formula of scutellarein is $C_{15}H_{10}O_6$ with a molecular weight of 286.24. Their structures are shown in FIG. 1.

Like most natural products from plants, baicalein and scutellarein are mainly prepared by chemical synthesis and organic solvent extraction. Organic solvent extraction extracts ingredient from the tissues of *Scutellaria baicalensis* Georgi, *Erigeron breviscapus, Scutellaria barbata* and other medicinal plants, which needs a lot of organic solvents and complex separation process. Therefore, the cost of organic solvent extraction is high. In addition, the main problems are that plants grow slow and medicinal resources are destroyed. Although baicalein and scutellarein can also be obtained in large quantities through chemical synthesis, the raw materials in the synthesis process contain cinnamic acid or its derivatives, oxyphenol and other chemical substances, which to some extent limits its application in medicine and food field. In addition, toxic reagents and expensive chemical catalysts are also used in the synthesis process.

Synthetic biology is a discipline which integrates and assembles standardized biological components based on rational design to build an excellent artificial life system. As soon as synthetic biology was put forward, its ideas and design have a profound impact on the development of industrial microbial technology, which makes microbial technology play a greater role in the development and production of drugs, biofuels and fine chemicals.

In the art, the synthetic elements of various natural products are assembled to conduct heterologous synthesis in microorganisms. However, the two flavonoids baicalein and scutellarein have not been successfully heterologously synthesized in microorganisms. Therefore, it is urgent to construct a microbial strain capable of heterologous synthesis of baicalein and scutellarein.

SUMMARY

Provided are a baicalein- and scutellarein-synthesizing microorganism, a preparation method for same, and applications thereof.

The first aspect of the present disclosure provides a method of producing baicalein and scutellarein, comprising: (1) introducing into a host cell genes expressing flavone 6-hydroxylase (F6H) and cytochrome P450 oxidoreductase (CPR), as well as genes for synthesizing chrysin or apigenin; and (2) culturing the host cell in a culture system containing phenylalanine and/or tyrosine to produce baicalein or scutellarein.

In a preferable example, the genes for synthesizing chrysin or apigenin comprises: genes expressing phenylalanine ammonia-lyase (PAL), 4-coumarate: CoA ligase (4CL), chalcone synthase (CHS), chalcone isomerase (CHI) and flavone synthase I (FNSI). Preferably, when introduced into the host cell, the genes expressing PAL, 4CL, CHS, CHI and FNSI are in the same expression vector.

In another preferable example, the flavone 6-hydroxylase is derived from *Scutellaria baicalensis*, including its homologues (homologous genes or peptides from other species); the CPR is derived from *Arabidopsis thaliana*, including its homologues.

In another preferable example, the PAL is derived from *Rhodotorula toruloides*, including its homologues; the 4CL is derived from *Petroselium crispum*, including its homologues; the CHS is derived from *Petunia X hybrida*, including its homologues; the CHI is derived from *Medicago sativa*, including its homologues; and the FNS I is derived from *Petroselium crispum*, including its homologues.

The another aspect of the present disclosure provides a method of producing baicalein and scutellarein, comprising: (1) introducing into a host cell genes expressing flavone 6-hydroxylase (F6H) and cytochrome P450 oxidoreductase (CPR) to obtain recombinant host cell; and (2) culturing the recombinant host cell in a culture system containing chrysin or apigenin to produce baicalein or scutellarein.

In another aspect of the disclosure, a method for converting chrysin or apigenin into baicalein or scutellarein is provided: catalyzing chrysin or apigenin by flavone 6-hydroxylase and cytochrome P450 oxidoreductase, thereby adding a hydroxyl group to the structure of chrysin or apigenin to form baicalein or scutellarein.

In a preferable embodiment, the flavone 6-hydroxylase (F6H) is a mutant flavone 6-hydroxylase with the N-terminal amino acids (1-10) to (20-30) truncated; preferably, it is a mutant flavone 6-hydroxylase with the N-terminal amino acids (2-5) to (22-28) truncated.

In another preferable embodiment, the flavone 6-hydroxylase is fused with a peptide tag, and the peptide tag is selected from N-terminal 8 amino acid peptide of bovine calf serum 17 hydroxylase (8RP), small ubiquitin-related modifier (Sumo), maltose binding protein (MBP), 2B1 family soluble protein of cytochrome P450 (2B1), or a combination thereof, preferably the peptide tag is maltose binding protein or 2B1 family soluble protein of cytochrome P450, or a combination thereof; preferably, the peptide tag is located at the N-terminal.

In another preferable embodiment, the cytochrome P450 oxidoreductase (CPR) is a mutant cytochrome P450 oxidoreductase with the N-terminal amino acids (1-20) to (60-85) truncated; preferably, it is a mutant cytochrome P450 oxidoreductase with the N-terminal amino acids (2-10) to (65-80) truncated; more preferably, it is a mutant cytochrome P450 oxidoreductase with the N-terminal amino acids (2-5)-(70-75) truncated.

In another preferable embodiment, the host cell includes: prokaryotic cell or eukaryotic cell; preferably, the prokaryotic cell includes: *Escherichia coli* cell, *Bacillus subtilis* cell; the eukaryotic cell includes: yeast cell.

Another aspect of the present disclosure provides a recombinant host cell comprising exogenous genes expressing flavone 6-hydroxylase and cytochrome P450 oxidoreductase.

In another preferable embodiment, the recombinant host cell also includes exogenous genes for synthesizing chrysin or apigenin.

In another preferable embodiment, the peptide tag is a single copy or 2-10 copies (such as 3, 4, 5, 6, 8 copies) of tandem sequences.

Another aspect of the present disclosure provides the use of any of the above recombinant host cells in the production of baicalein and scutellarein.

In one preferable embodiment, for the strain which does not comprise chrysin or apigenin synthesis gene(s) in the cell, the use is to produce baicalein and scutellarein with exogenous chrysin or apigenin as the substrate; for the strain which comprises chrysin or apigenin synthesis gene(s) in the cell, the use is to produce baicalein and scutellarein in the presence of exogenous phenylalanine and/or tyrosine.

Another aspect of the disclosure provides a method of preparing a host cell for producing baicalein and scutellarein, comprising: introducing genes expressing flavone 6-hydroxylase and cytochrome P450 oxidoreductase into the host cell to obtain a recombinant strain; preferably, the method also comprises: introducing genes for synthesizing chrysin or apigenin.

In another aspect of the present disclosure, a kit for the production of baicalein and scutellarein is provided, wherein the kit comprises any of the above recombinant host cells.

In another preferable embodiment, the kit also comprises: culture medium for the host cell, instruction for use, etc.

In another aspect of the present disclosure, a mutant flavonoid 6-hydroxylase is provided, which corresponds to the wild-type flavonoid 6-hydroxylase (F6H) but the N-terminal amino acids (1-10) to (20-30) are truncated; preferably, the N-terminal amino acids (2-5) to (22-28) are truncated; more preferably, the mutant flavonoid 6-hydroxylase has the amino acid sequence shown in SEQ ID NO: 2.

In another aspect of the present disclosure, a mutant cytochrome P450 oxidoreductase is provided, which corresponds to the wild-type cytochrome P450 oxidoreductase but the N-terminal amino acids (1-20) to (60-85) are truncated; preferably, the N-terminal amino acids (2-10) to (65-80) are truncated; more preferably, the N-terminal amino acids (2-5) to (70-75) are truncated; preferably, the mutant cytochrome P450 oxidoreductase has the amino acid sequence shown in SEQ ID NO: 8.

In another aspect of the present disclosure, a fusion polypeptide is provided, which comprises any of the above mutant flavone 6-hydroxylase fused with a peptide tag, the peptide tag is selected from the group consisting of: 8RP, Sumo, MBP, 2B1; preferably is MBP or 2B1.

In a preferable embodiment, the fusion polypeptide has an amino acid sequence selected from the group consisting of: SEQ ID NO: 3, SEQ ID NO: 4, SEQ ID NO: 5 or SEQ ID NO: 6.

In another aspect of the present disclosure, a polynucleotide is provided, which encodes: the mutant flavonoid 6-hydroxylase; or the mutant cytochrome P450 oxidoreductase; or the fusion polypeptide.

In another aspect of the present disclosure, an expression construct is provided, which comprises: any of the above polynucleotides; or polynucleotides encoding any of the mutant flavonoid 6-hydroxylase or the fusion protein described above, and polynucleotides encoding the mutant cytochrome P450 oxidoreductase described above.

In another preferable embodiment, the expression construct also comprises promoter and terminator operably linked with the above polynucleotide.

Another aspect of the disclosure provides the use of the mutant flavonoid 6-hydroxylase or the fusion protein and the mutant cytochrome P450 oxidoreductase in production of baicalein or scutellarein by adding a hydroxyl group to the structure of chrysin or apigenin.

Other aspects of the disclosure will be apparent to those skilled in the art based on the disclosure herein.

Figure 1:
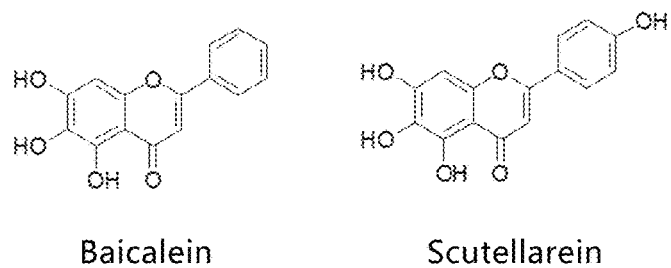
FIG. 1. Structural formula of baicalein and scutellarein.
Figure 2:
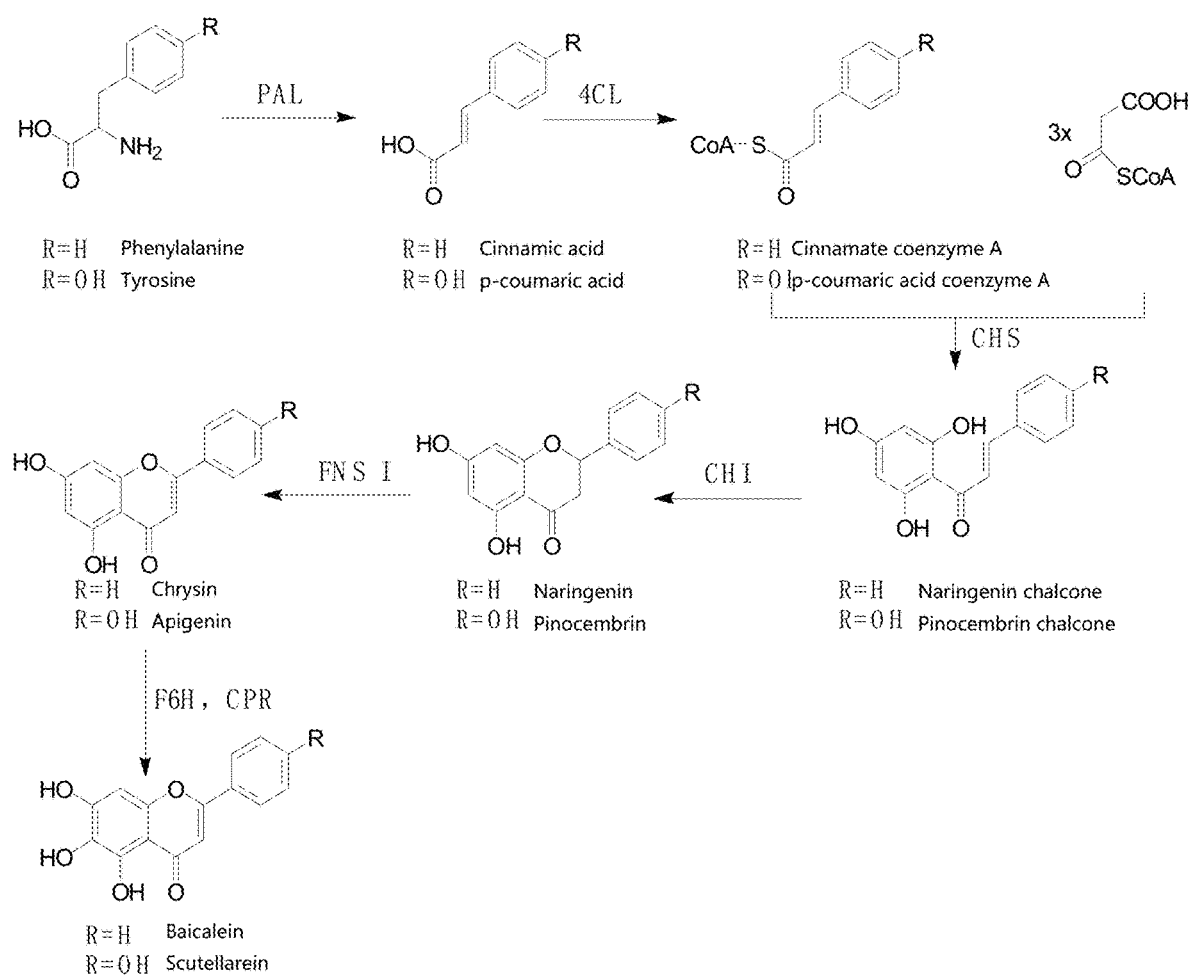
FIG. 2. Schematic of biosynthesis pathway of baicalein and scutellarein.

A. Schematic of the key elements in the constructed plasmid;

B. The conversion rates of baicalein from chrysin in recombinant *E. coli;*

C. HPLC results of the catalytic reaction solution of recombinant *E. coli*. Chr: chrysin; Bai: baicalein.

DETAILED DESCRIPTION

The inventor is committed to the heterologous synthesis of baicalein and scutellarein from microorganisms, and to improving biological production of baicalein and scutellarein. After in-depth study, engineering strains with high yield of baicalein and scutellarein is obtained by modifying the heterologous metabolic pathway of host cells through genetic engineering.

As used herein, "N-terminal amino acids (1-10) to (20-30)" refers to a sequence starting from any amino acid in N-terminal amino acids 1-10 and ending at any amino acid in N-terminal amino acids 20-30.

As used herein, "N-terminal amino acids (2-5) to (22-28)" refers to a sequence starting from any amino acid in N-terminal amino acids 2-5 and ending at any amino acid in N-terminal amino acids 22-28.

As used herein, "N-terminal amino acids (1-20) to (60-85)" refers to a sequence starting from any amino acid in N-terminal amino acids 1-20 and ending at any amino acid in N-terminal amino acids 60-85.

As used herein, "N-terminal amino acids (2-10) to (65-80)" refers to a sequence starting from any amino acid in N-terminal amino acids 2-10 and ending at any amino acid in N-terminal amino acids 65-80.

As used herein, "N-terminal amino acids (2-5) to (70-75)" refers to a sequence starting from any amino acid in N-terminal amino acids 2-5 and ending at any amino acid in N-terminal amino acids 70-75.

As used herein, "exogenous" or "heterologous" refers to two or more nucleic acid or protein sequences from different sources.

As used herein, "operably linked (to)" or "operably connected (to)" is intended to mean a functional spatial arrangement between two or more nucleic acid regions or nucleic acid sequences. For example, a promoter region is "operatively linked" to the nucleic acid sequence of a target gene when the promoter region is placed at a specific position relative to the nucleic acid sequence so that the transcription of the nucleic acid sequence is guided by the promoter region.

As used herein, the "expression construct" refers to a recombinant DNA molecule that contains the desired nucleic acid coding sequence. An expression construct may contain one or more gene expression cassettes. The "construct" is usually contained in an expression vector.

As used herein, the PAL, 4CL, CHS, CHI and FNSI proteins are proteins that constitute the biosynthesis pathway of chrysin or apigenin in the expression system.

As used herein, the F6H and CPR proteins are the proteins that convert chrysin or apigenin into baicalein or scutellarein in the expression system.

Wild types of the above proteins or genes have been identified in the art, so they can be available and prepared from the public. As a preferable embodiment of the disclosure, PAL is derived from *Rhodotorula toruloides*, with the sequence shown in GenBank accession number AAA33883.1; 4CL is derived from *Petroselium crispum*, with the sequence shown in GenBank accession number KF765780.1; CHS is derived from *Petunia X hybrida*, with the sequence shown in GenBank accession number KF765781.1; CHI is derived from *Medicago sativa*, with the sequence shown in GenBank accession number KF765782.1; FNS I is derived from *Petroselium crispum*, with the sequence shown in Swiss-Prot accession number Q7XZQ8.1.

Wild types of F6H and CPR have also been identified in the art. As a preferable embodiment of the disclosure, F6H is derived from *Scutellaria baicalensis*, with the sequence shown in GenBank accession number ASW21050.1. As a preferable embodiment of the disclosure, CPR is derived from *Arabidopsis thaliana*, with the sequence shown in GenBank accession number NP_849472.2.

The inventor found that when using host cells to produce baicalein and scutellarein, the wild-type F6H can only produce a small amount of products, which cannot achieve large-scale production. Through modification of multiple proteins involved in the reaction and a large number of screening and analysis, optimized modification schemes were obtained, which greatly improved the yield of baicalein and scutellarein of microorganisms, especially prokaryotic expression systems such as *E. coli*.

Therefore, a preferable embodiment of the present disclosure provides a mutant F6H that corresponds to the wild-type F6H with N-terminal amino acids (1-10) to (20-30) truncated; preferably, it is a mutant F6H with N-terminal amino acids (2-5) to (22-28) truncated; more preferably, it is a mutant F6H with N-terminal amino acids 2 to 25 truncated.

In a preferable embodiment of the disclosure, a fusion protein containing F6H or mutant F6H is provided, which includes F6H or any mutant F6H, and a peptide tag fused therewith, wherein the peptide tag is selected from the group consisting of 8RP, Sumo, MBP, 2B1, or a combination of them; preferably is MBP or 2B1. The peptide tag and the F6H or mutant F6H may or may not contain a linker peptide, and the linker peptide does not affect their biological activities.

In a preferable embodiment of the present disclosure, a mutant CPR is provided, which corresponds to the wild-type CPR with N-terminal amino acids (1-20) to (60-85) truncated; preferably, it is a mutant CPR with N-terminal amino acids (2-10) to (65-80) truncated; more preferably, it is a mutant CPR with N-terminal amino acids (2-5) to (70-75) truncated.

In addition to the above preferable proteins (including the above wild-type proteins and mutant proteins), the disclosure also includes their bioactive fragments, derivatives and analogues. Their fragments, derivatives or analogues may comprise deletion, insertion and/or substitution of several (usually 1-50, more preferably 1-20, yet more preferably 1-10, 1-5, 1-3, or 1-2) amino acids, as well as addition or deletion of one or more (for example, less than 100, 80, 50, 20, more preferably less than 10, yet more preferably less than 5) amino acids at C-terminal and/or N-terminal. For example, substitution with amino acids of comparable or similar properties usually does not change protein function in the art. As another example, addition of deletion of one or more amino acids to the C-terminus and/or N-terminus usually does not change the function of a protein either. However, for further variation of the above mutant protein, the N-terminal was truncated as described above.

In addition to the above preferable proteins (including the above wild-type proteins and mutant proteins), the disclosure also includes their analogues. The differences between analogs and the original protein may be the difference in amino acid sequences, and may also be the difference in the forms of modifications that will not affect the sequence, or both. These proteins include natural or induced genetic variants. Induced variants can be obtained by a variety of techniques, such as generating random mutagenesis by irradiation or exposure to mutagens, and can also be obtained by directed mutagenesis or other known molecular biology techniques. Analogs mentioned herein also include analogs with residue(s) different from natural L-amino acid (e.g., D-amino acids), as well as analogs with a non-naturally occurred or synthetic amino acid (such as β, γ-amino acids). It should be understood that the proteins of the present disclosure are not limited to the representative proteins described above.

In addition to the above preferable proteins (including the above wild-type proteins and mutant proteins), the disclosure also includes the protein with high homology (for example, having 70% or higher, preferable 80% or higher, more preferable 90% or higher (such as 95%, 98% or 99%) homology with the sequence of the particular described protein) and having the same function as the corresponding protein.

The disclosure describes proteins or genes from specific species. It should be understood that although the proteins or genes obtained from a specific species are preferably studied in the present disclosure, other proteins or genes obtained from other species and having high homology (such as having more than 60%, such as 70%, 80%, 85%, 90%, 95%, or even 98% sequence identity) with the proteins or genes also fall within the scope of the present disclosure.

The disclosure also provides a polynucleotide sequence encoding the protein of the disclosure or a conserved variant thereof. The polynucleotide sequences herein can be in the form of DNA or RNA. Forms of DNA include cDNA, genomic DNA or artificially synthesized DNA. DNA can be single-stranded or double-stranded. The DNA may be coding strand or non-coding strand. The polynucleotide encoding the mutant mature protein of the disclosure includes: the coding sequence only encoding the mature protein; the coding sequence encoding the mature protein and a various additional coding sequence; the coding sequence encoding the mature protein (and an optional additional coding sequence) and a noncoding sequence.

The disclosure also includes the codon-optimized polynucleotide sequence of the gene sequence, for example, the codon-optimized according to the codon bias of the host cell.

In the disclosure, an engineering strain with high yield of baicalein and scutellarein is also constructed, which includes exogenous genes expressing F6H (especially the mutant F6H or fusion protein) and CPR (especially the mutant CPR or fusion protein). Baicalein or scutellarein can be produced by culturing the recombinant strain and adding chrysin or apigenin into the culture system.

In the disclosure, another engineering strain with high yield of baicalein and scutellarein is constructed, which includes exogenous genes expressing F6H (especially the mutant F6H or fusion protein) and CPR (especially the mutant CPR or fusion protein), as well as genes for synthesizing chrysin or apigenin. The genes for synthesizing chrysin or apigenin comprise genes expressing PAL, 4CL, CHS, CHI and FNSI proteins.

By use of the strain according to the disclosure, which has great stability, large-scale cultivation and production of baicalein or scutellarein in a bioreactor can be realized. The yield of baicalein or scutellarein of the optimized strain of the disclosure is very high.

In the disclosure, more economical and convenient manufacture of baicalein or scutellarein can be conducted by production of baicalein or scutellarein from E. coli.

The disclosure also provides a kit for producing baicalein or scutellarein engineering strains. In addition, it can also include culture medium for E. coli, separation or detection reagent for baicalein or scutellarein, instruction for use, etc.

The disclosure is further illustrated by the specific examples described below. It should be understood that these examples are merely illustrative, and do not limit the scope of the present disclosure. The experimental methods without specifying the specific conditions in the following examples generally used the conventional conditions, such as those described in J. Sambrook, Molecular Cloning: A Laboratory Manual (3rd ed. Science Press, 2002) or followed the manufacturer's recommendation.

Experimental Materials

AxyPrep Total RNA Miniprep Kit, PCR Gel Extraction Kit, Plasmid Extraction Kit are from Axygen; PrimeScript RT reagent Kit with gDNA Eraser (Perfect Real Time), PrimeSTAR Max DNA Polymerase are from Takara, and restriction enzymes are from NEB.

E. coli DH10B was used for gene cloning, E. coli BL21 (DE3) was used for protein expression and baicalein and scutellarein production. pET28a, pEDDuet-1 and pCDF-Duet-1 vectors were used for assembling of genes in metabolic pathway.

Baicalein and scutellarein standards were purchased from Shanghai Yuanye Biotechnology Co., Ltd. Other reagents are analytical grade reagent or chromatographic grade reagent, purchased from Sinopharm Chemical Reagent Co., Ltd.

PCR was conducted on Arktik Thermal Cycler (Thermo Fisher Scientific); ZXGP-A2050 Incubator and ZWY-211G Constant Temperature Oscillator were used for culture; high-speed freezing Centrifuge 5418R and Centrifuge 5418 (Eppendorf) were used for centrifugation. Vacuum concentration was performed with Concentrator Plus (Eppendorf); $OD_{600}$ was detected using UV-1200 Ultraviolet/Visible Spectrophotometer (Shanghai Mapada Instrument Co., Ltd.). Rotary evaporation system consists of IKA RV 10 Digital Rotary Evaporator (IKA), MZ 2C NT Chemical Diaphragm Pump and CVC3000 vacuum controller (Vacuubrand). Dionex UltiMate 3000 Liquid Chromatography System (Thermo Fisher Scientific) was used for HPLC.

Liquid phase detection conditions: A phase: 0.1% formic acid solution, B phase: acetonitrile; separation conditions: 0-20 min, 20% B phase-55% B phase, 20-22 min, 55% B phase-100% B phase, 22-27 min, 100% B phase-20% B phase, 27-35 min, 100% B phase-20% B phase, 35-40 min, 20% B phase; detection wavelength: 340 nm, column temperature: 30° C. The chromatographic column was Thermo syncronis C18 RP column (250 mm*4.6 mm, 5 μm).

Example 1. Polypeptide and its Sequence Optimization

1. Optimization of F6H Polypeptide Sequence

The sequence of *Scutellaria baicalensis* F6H (SbF6H, 517aa, Genbank access No. ASW21050.1) is:

MELSSVIYGAIALLSLFYCYLHFSKPKKSSLNAPPEAGGARFITGHLHLM

DGRSASDKLPHINLGLLADQHGPIFTIRLGVHRAVVVSSWELAKEIFTTH

DTAVMARPRLIADDYLSYDGASLGFSPYGPYWREIRKLVTTELLSARRIE

LQRATRVREITQFTGELYKLWEEKKDGSGRVLVDMKQWLGNLSLNLVSRM

VVGKRFYGGDDSETTKRWRGVMREFFQLIGQFIPGDGLPFLRWLDLGGFE

KRTRDTAYELDKIIAMWLAEYRKREYSGDDKEQCFMALMLSLVQANPTLQ

LHYDADTIIKATCQVLISAASDTTTVILIWVISLLLNNADVLKKVQEELD

EQVGRERRVEESDISNLPYLQAVVKETMRLYPPAPFAGVRAFSEDCTVGG

YHIQKGTFLIVNLWKLHRDPRVWSDDALEFKPQRFFDKKVEVKGQDFELM

-continued

PFGGGRRMCPGSNLGMHMVHFVLANILQAFDITTGSTVDMTESVGLTNMK

ATPLDAILTPRLSPTLY*

Modification 1: the modified F6H mutant trF6H was constituted by removing the amino acids 2-25 of SEQ ID NO: 1 and adding two amino acids MA to the N-terminal. The sequence of trF6H is as follows (SEQ ID NO: 2):

<u>MA</u>MPKKSSLNAPPEAGGARFITGHLHLMDGRSASDKLPHINLGLLADQHG

PIFTIRLGVHRAVVVSSWELAKEIFTTHDTAVMARPRLIADDYLSYDGAS

LGFSPYGPYWREIRKLVTTELLSARRIELQRATRVREITQFTGELYKLWE

EKKDGSGRVLVDMKQWLGNLSLNLVSRMVVGKRFYGGDDSETTKRWRGVM

REFFQLIGQFIPGDGLPFLRWLDLGGFEKRTRDTAYELDKIIAMWLAEYR

KREYSGDDKEQCFMALMLSLVQANPTLQLHYDADTIIKATCQVLISAASD

TTTVILIWVISLLLNNADVLKKVQEELDEQVGRERRVEESDISNLPYLQA

VVKETMRLYPPAPFAGVRAFSEDCTVGGYHIQKGTFLIVNLWKLHRDPRV

WSDDALEFKPQRFFDKKVEVKGQDFELMPFGGGRRMCPGSNLGMHMVHFV

LANILQAFDITTGSTVDMTESVGLTNMKATPLDAILTPRLSPTLY*

Modification 2: the modified F6H mutant 8RPtrF6H was constituted by removing the amino acids 2-25 of SEQ ID NO: 1 and adding amino acids of 8RP to the N-terminal. The sequence of 8RPtrF6H is as follows (SEQ ID NO: 3):

<u>MALLLAVFM</u>PKKSSLNAPPEAGGARFITGHLHLMDGRSASDKLPHINLGL

LADQHGPIFTIRLGVHRAVVVSSWELAKEIFTTHDTAVMARPRLIADDYL

SYDGASLGFSPYGPYWREIRKLVTTELLSARRIELQRATRVREITQFTGE

LYKLWEEKKDGSGRVLVDMKQWLGNLSLNLVSRMVVGKRFYGGDDSETTK

RWRGVMREFFQLIGQFIPGDGLPFLRWLDLGGFEKRTRDTAYELDKIIAM

WLAEYRKREYSGDDKEQCFMALMLSLVQANPTLQLHYDADTIIKATCQVL

ISAASDTTTVILIWVISLLLNNADVLKKVQEELDEQVGRERRVEESDISN

LPYLQAVVKETMRLYPPAPFAGVRAFSEDCTVGGYHIQKGTFLIVNLWKL

HRDPRVWSDDALEFKPQRFFDKKVEVKGQDFELMPFGGGRRMCPGSNLGM

HMVHFVLANILQAFDITTGSTVDMTESVGLTNMKATPLDAILTPRLSPTL

Y*

Modification 3: the modified F6H mutant SumotrF6H was constituted by removing the amino acids 2-25 of SEQ ID NO: 1 and adding amino acids of Sumo to the N-terminal. The sequence of SumotrF6H is as follows (SEQ ID NO: 4):

<u>MADSEVNQEAKPEVKPEVKPETHINLKVSDGSSEIFFKIKKTTPLRRLME</u>

<u>AFAKRQGKEMDSLRFLYDGIRIQADQTPEDLDMEDNDIIEAHREQIGGMP</u>

KKSSLNAPPEAGGARFITGHLHLMDGRSASDKLPHINLGLLADQHGPIFT

IRLGVHRAVVVSSWELAKEIFTTHDTAVMARPRLIADDYLSYDGASLGFS

PYGPYWREIRKLVTTELLSARRIELQRATRVREITQFTGELYKLWEEKKD

GSGRVLVDMKQWLGNLSLNLVSRMVVGKRFYGGDDSETTKRWRGVMREFF

QLIGQFIPGDGLPFLRWLDLGGFEKRTRDTAYELDKIIAMWLAEYRKREY

SGDDKEQCFMALMLSLVQANPTLQLHYDADTIIKATCQVLISAASDTTTV

ILIWVISLLLNNADVLKKVQEELDEQVGRERRVEESDISNLPYLQAVVKE

TMRLYPPAPFAGVRAFSEDCTVGGYHIQKGTFLIVNLWKLHRDPRVWSDD

ALEFKPQRFFDKKVEVKGQDFELMPFGGGRRMCPGSNLGMHMVHFVLANI

LQAFDITTGSTVDMTESVGLTNMKATPLDAILTPRLSPTLY*

Modification 4: the modified F6H mutant MBPtrF6H was constituted by removing the amino acids 2-25 of SEQ ID NO: 1 and adding amino acids of MBP to the N-terminal. The sequence of MBPtrF6H is as follows (SEQ ID NO: 5):

<u>MAKIEEGKLVIWINGDKGYNGLAEVGKKFEKDTGIKVTVEHPDKLEEKFP</u>

<u>QVAATGDGPDIIFWAHDRFGGYAQSGLLAEITPDKAFQDKLYPFTWDAVR</u>

<u>YNGKLIAYPIAVEALSLIYNKDLLPNPPKTWEEIPALDKELKAKGKSALM</u>

<u>FNLQEPYFTWPLIAADGGYAFKYENGKYDIKDVGVDNAGAKAGLTFLVDL</u>

<u>IKNKHMNADTDYSIAEAAFNKGETAMTINGPWAWSNIDTSKVNYGVTVLP</u>

<u>TFKGQPSKPFVGVLSAGINAASPNKELAKEFLENYLLTDEGLEAVNKDKP</u>

<u>LGAVALKSYEEELVKDPRIAATMENAQKGEIMPNIPQMSAFWYAVRTAVI</u>

<u>NAASGRQTVDEALKDAQT</u>MPKKSSLNAPPEAGGARFITGHLHLMDGRSAS

DKLPHINLGLLADQHGPIFTIRLGVHRAVVVSSWELAKEIFTTHDTAVMA

RPRLIADDYLSYDGASLGFSPYGPYVVREIRKLVTTELLSARRIELQRAT

RVREITQFTGELYKLWEEKKDGSGRVLVDMKQWLGNLSLNLVSRMVVGKR

FYGGDDSETTKRWRGVMREFFQLIGQFIPGDGLPFLRWLDLGGFEKRTRD

TAYELDKIIAMWLAEYRKREYSGDDKEQCFMALMLSLVQANPTLQLHYDA

DTIIKATCQVLISAASDTTTVILIWVISLLLNNADVLKKVQEELDEQVGR

ERRVEESDISNLPYLQAVVKETMRLYPPAPFAGVRAFSEDCTVGGYHIQK

GTFLIVNLWKLHRDPRVWSDDALEFKPQRFFDKKVEVKGQDFELMPFGGG

RRMCPGSNLGMHMVHFVLANILQAFDITTGSTVDMTESVGLTNMKATPLD

AILTPRLSPTLY*

Modification 5: the modified F6H mutant 2B1trF6H was constituted by removing the amino acids 2-25 of SEQ ID NO: 1 and adding amino acids of 2B1 to the N-terminal. The sequence of 2B1trF6H is as follows (SEO ID NO: 6):

<u>MAKKTSSKGKLPPGPSMP</u>KKSSLNAPPEAGGARFITGHLHLMDGRSASDK

LPHINLGLLADQHGPIFTIRLGVHRAVVVSSWELAKEIFTTHDTAVMARP

RLIADDYLSYDGASLGFSPYGPYVVREIRKLVTTELLSARRIELQRATRV

REITQFTGELYKLWEEKKDGSGRVLVDMKQWLGNLSLNLVSRMVVGKRFY

GGDDSETTKRWRGVMREFFQLIGQFIPGDGLPFLRWLDLGGFEKRTRDTA

YELDKIIAMWLAEYRKREYSGDDKEQCFMALMLSLVQANPTLQLHYDADT

IIKATCQVLISAASDTTTVILIWVISLLLNNADVLKKVQEELDEQVGRER

RVEESDISNLPYLQAVVKETMRLYPPAPFAGVRAFSEDCTVGGYHIQKGT

FLIVNLWKLHRDPRVWSDDALEFKPQRFFDKKVEVKGQDFELMPFGGGRR

-continued

MCPGSNLGMHMVHFVLANILQAFDITTGSTVDMTESVGLTNMKATPLDAI

LTPRLSPTLY*

2. Modification of CPR

The sequence of *Arabidopsis thaliana* CPR (AtCPR, 712aa, Genebank access No. NP_849472.2) is as follows (SEQ ID NO: 7):

MSSSSSSSTSMIDLMAAIIKGEPVIVSDPANASAYESVAAELSSMLIENR

QFAMIVTTSIAVLIGCIVMLVWRRSGSGNSKRVEPLKPLVIKPREEEIDD

GRKKVTIFFGTQTGTAEGFAKALGEEAKARYEKTRFKIVDLDDYAADDDE

YEEKLKKEDVAFFFLATYGDGEPTDNAARFYKWFTEGNDRGEWLKNLKYG

VFGLGNRQYEHFNKVAKVVDDILVEQGAQRLVQVGLGDDDQCIEDDFTAW

REALWPELDTILREEGDTAVATPYTAAVLEYRVSIHDSEDAKFNDINMAN

GNGYTVFDAQHPYKANVAVKRELHTPESDRSCIHLEFDIAGSGLTYETGD

HVGVLCDNLSETVDEALRLLDMSPDTYFSLHAEKEDGTPISSSLPPPFPP

CNLRTALTRYACLLSSPKKSALVALAAHASDPTEAERLKHLASPAGKVDE

YSKWVVESQRSLLEVMAEFPSAKPPLGVFFAGVAPRLQPRFYSISSSPKI

AETRIHVTCALVYEKMPTGRIHKGVCSTWMKNAVPYEKSENCSSAPIFVR

QSNFKLPSDSKVPIIMIGPGTGLAPFRGFLQERLALVESGVELGPSVLFF

GCRNRRMDFIYEEELQRFVESGALAELSVAFSREGPTKEYVQHKMMDKAS

DIWNMISQGAYLYVCGDAKGMARDVHRSLHTIAQEQGSMDSTKAEGFVKN

LQTSGRYLRDVW*

The modified AtCPR mutant trAtCPR was constituted by removing the amino acids 2-72 of SEQ ID NO: 7. The sequence of trAtCPR is as follows (SEQ ID NO: 8):

MRRSGSGNSKRVEPLKPLVIKPREEEIDDGRKKVTIFFGTQTGTAEGFAK

ALGEEAKARYEKTRFKIVDLDDYAADDDEYEEKLKKEDVAFFFLATYGDG

EPTDNAARFYKWFTEGNDRGEWLKNLKYGVFGLGNRQYEHFNKVAKVVDD

ILVEQGAQRLVQVGLGDDDQCIEDDFTAWREALWPELDTILREEGDTAVA

TPYTAAVLEYRVSIHDSEDAKFNDINMANGNGYTVFDAQHPYKANVAVKR

ELHTPESDRSCIHLEFDIAGSGLTYETGDHVGVLCDNLSETVDEALRLLD

MSPDTYFSLHAEKEDGTPISSSLPPPFPPCNLRTALTRYACLLSSPKKSA

LVALAAHASDPTEAERLKHLASPAGKVDEYSKWVVESQRSLLEVMAEFPS

AKPPLGVFFAGVAPRLQPRFYSISSSPKIAETRIHVTCALVYEKMPTGRI

HKGVCSTWMKNAVPYEKSENCSSAPIFVRQSNFKLPSDSKVPIIMIGPGT

GLAPFRGFLQERLALVESGVELGPSVLFFGCRNRRMDFIYEEELQRFVES

GALAELSVAFSREGPTKEYVQHKMMDKASDIWNMISQGAYLYVCGDAKGM

ARDVHRSLHTIAQEQGSMDSTKAEGFVKNLQTSGRYLRDVW*

Example 2. Construction of Recombinant Plasmid Containing Novel F6H Mutant

Based on pETDuet-1, plasmid pYH45 was constituted by linking AtCPR into NdeI and XhoI sites by one-step cloning method.

Based on pETDuet-1, plasmid pYH46 was constituted by linking trAtCPR into NdeI and XhoI sites by one-step cloning method.

Furthermore, pUC19-F6H was constituted by linking the codon optimized coding sequence of F6H (synthesized by GenScript) into pUC19. PCR was conducted using F6H-F/R as primers and pUC19-F6H as templates. The PCR system was 50 μL (Primestar Max Premix, 25 μL; final concentration 0.2-0.3 μM of the two primers; pUC19-F6H, 0.2 μL; the remaining volume was supplemented with sterilized distilled water). PCR reaction procedure is: pre-denaturation at 98° C. for 2 min, denaturation at 98° C. for 10 s, annealing at 55° C. for 15 s, extension at 72° C. for 20 s, 25 cycles. The amplified fragment of about 1.5 kb was detected by agarose electrophoresis, purified and digested with Nco I and BamH I. The digested fragment was ligated into pYH46 digested by the same enzymes, and the ligated product was transformed into competent cells of *E. coli* DH10B. The plasmid was extracted. The recombinant plasmid pYH59 was verified by double digestion (on restriction sites introduced during plasmid construction) and gene sequencing. Similarly, the digested fragment was ligated into pYH45 to obtain the recombinant plasmid pYH59.

PCR was conducted using trF6H-F/F6H-R as primers and pUC19-trF6H as templates. Plasmid pYH58 was obtained by ligating the amplified fragment into NdeI and BamH I of pYH46 by one-step cloning method.

PCR was conducted using 8RP-trF6H-F/F6H-R as primers and pUC19-trF6H as templates. Plasmid pYH60 was obtained by ligating the amplified fragment into NdeI and BamH I of pYH46 by one-step cloning method.

DNA fragment containing Sumo sequence was amplified using pETSumo (Invitrogen) as templates and Sumo-F/Sumo-trF6H-R as primers. DNA fragment containing trF6H was amplified using pUC19-trF6H as templates and Sumo-trF6H-F/F6H-R as primers. PCR amplification was conducted using Sumo-F/F6H-R as primers and the above two DNA fragments as templates. Plasmid pYH61 was obtained by ligating the amplified fragment into NdeI and BamH I of pYH46 by one-step cloning method.

DNA fragments containing MBP sequence was amplified using pMAL-c5x (Invitrogen) as templates and MBP-F/MBP-trF6H-R as primers. DNA fragments containing trF6H was amplified using pUC19-trF6H as templates and MBP-trF6H-F/F6H-R as primers. Then PCR amplification was conducted using MBP-F/F6H-R as primers and the above two DNA fragments as templates. Plasmid pYH62 was obtained by ligating the amplified fragment into NdeI and BamH I of pYH46 by one-step cloning method.

PCR was conducted using 2B1-F/F6H-R as primers and pUC19-trF6H as templates. Plasmid pYH63 was obtained by ligating the amplified fragment into NdeI and BamH I of pYH46 by one-step cloning method.

PCR was conducted using trF6H-F/F6H-R as primers and pUC19-trF6H as templates. Plasmid pYH64 was obtained by ligating the amplified fragment into NdeI and BamH I of pYH45 by one-step cloning method.

DNA fragments containing MBP sequence was amplified using pMAL-c5x as templates and MBP-F/MBP-trF6H-R as primers. DNA fragments containing trF6H was amplified using pUC19-trF6H as templates and MBP-trF6H-F/F6H-R as primers. Then PCR amplification was conducted using MBP-F/F6H-R as primers and the above two DNA fragments as templates. Plasmid pYH65 was obtained by ligating the amplified fragment into NdeI and BamH I of pYH45 by one-step cloning method.

Figure 3:
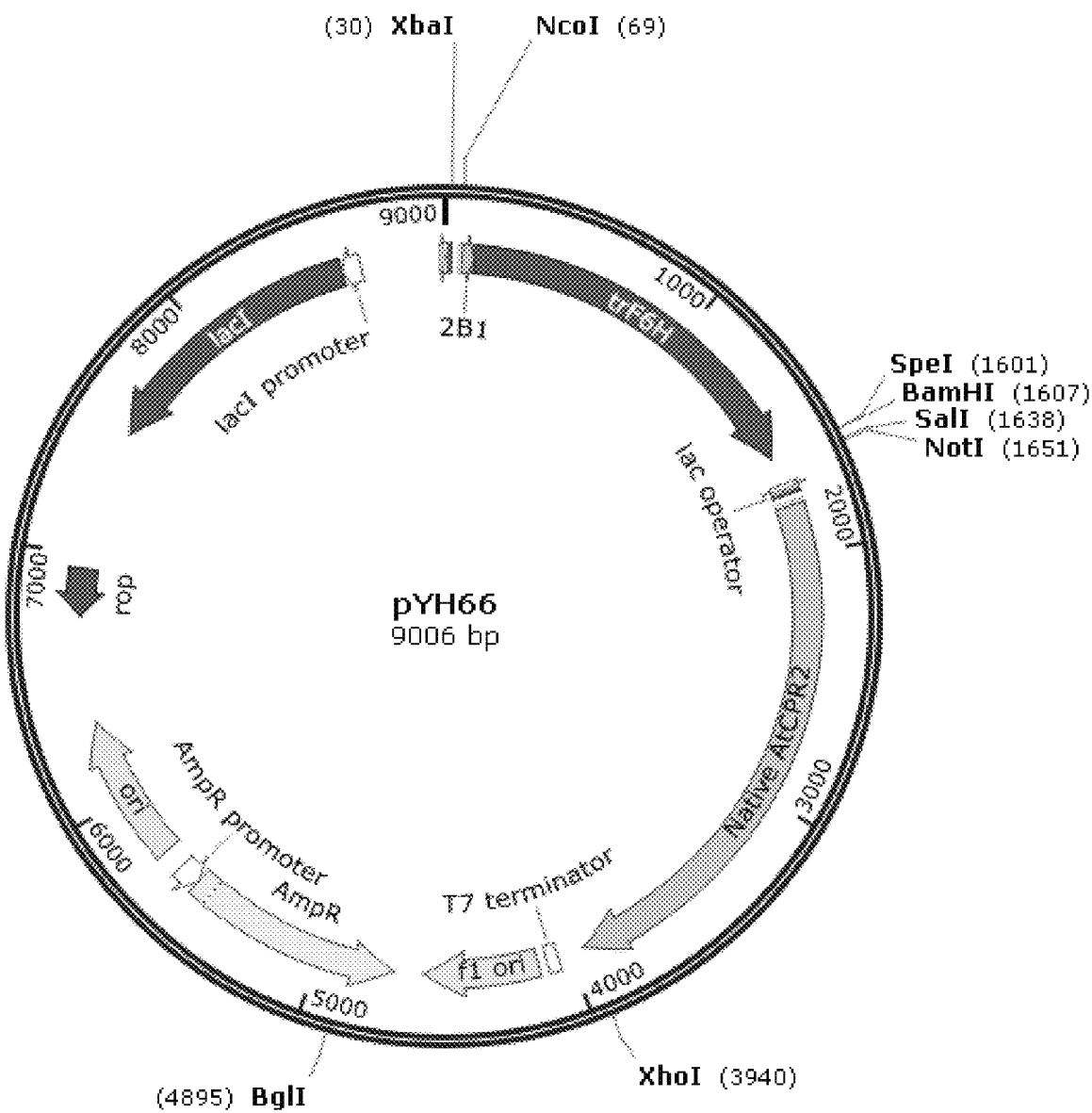
FIG. 3. Schematic of plasmid pYH66.

PCR was conducted using 2B1-F/F6H-R as primers and pUC19-2B1trF6H as templates. Plasmid pYH66 was obtained by ligating the amplified fragment into NdeI and BamH I of pYH45 by one-step cloning method. Schematic of plasmid pYH66 is shown in FIG. 3.

Figure 9:
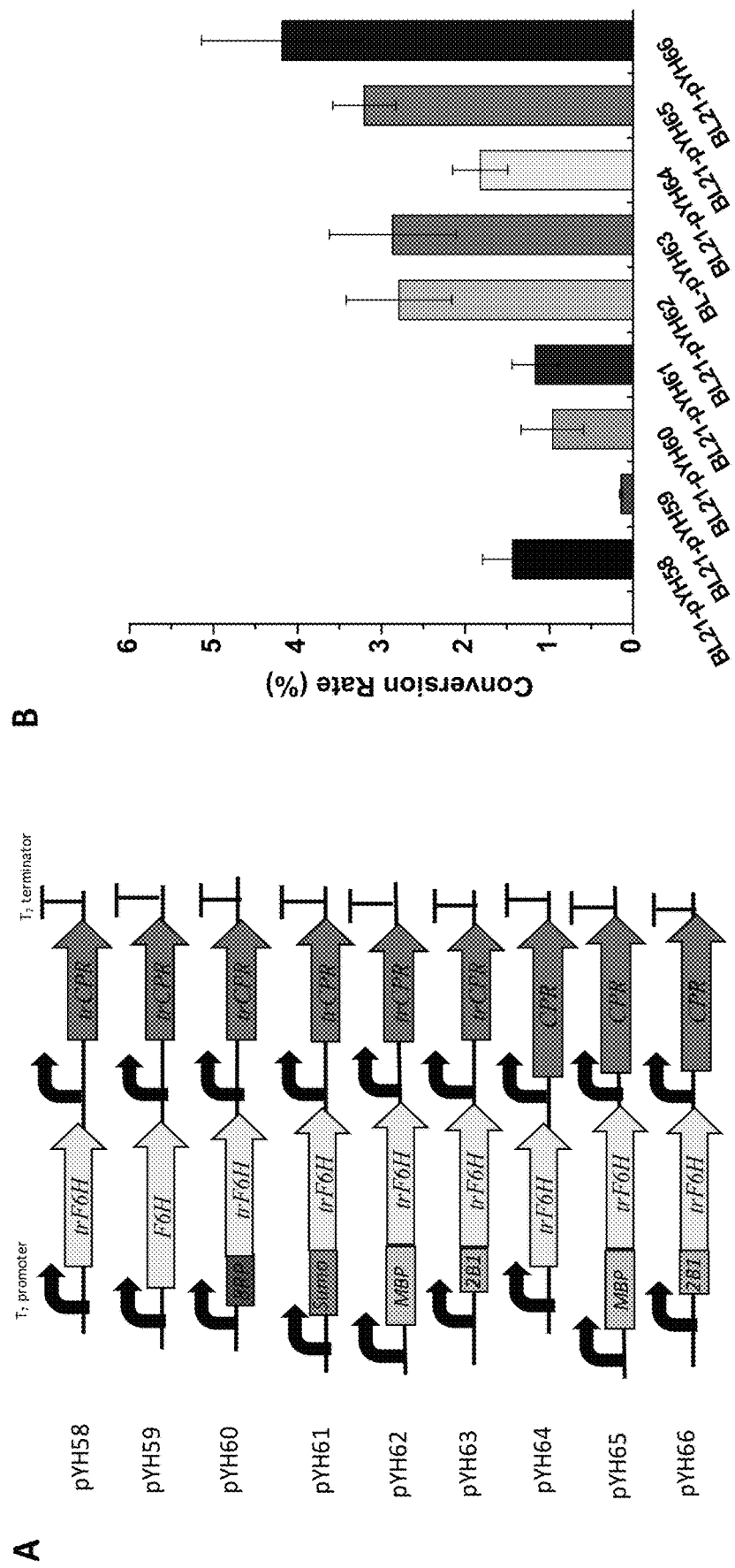
FIG. 9. Production of baicalein from chrysin catalyzed by SbF6H and AtCPR mutants.

The primers used in the above constructions are shown in Table 1. Schematic of the key elements in the constructed plasmid is shown in FIG. 9A.

TABLE 1

| Primers | Sequences |
|---|---|
| F6H-F | TATACCATGGAACTGAGCAGTGTGA (SEQ ID NO: 9) |
| F6H-R | CTCGAATTCGGATCCACTAGTTTAATATAAAGTCGG (SEQ ID NO: 10) |
| trF6H-F | CTTTAAGAAGGAGATATACCATGGCGATGCCGAAGAAAAGCTC (SEQ ID NO: 11) |
| 8RP-trF6H-F | CTTTAAGAAGGAGATATACCATGGCTCTGTTATTAGCAGTTTTTATGCCGAAGAAAAGCTCTT (SEQ ID NO: 12) |
| MBP-F | CTTTAAGAAGGAGATATACCATGGCTAAAATCGAAGAAG (SEQ ID NO: 13) |
| MBP-trF6H-F | CTGAAAGACGCGCAGACTATGCCGAAGAAAAGCTC (SEQ ID NO: 14) |
| MBP-trF6H-R | GAGCTTTTCTTCGGCATAGTCTGCGCGTCTTTCAG (SEQ ID NO: 15) |
| 2B1-F | CTTTAAGAAGGAGATATACCATGGCTAAGAAAACGAGCTCTAAAGGGAAGCTCCCACCAGGACCTAGCATGCCGAAGAAAAGCTCTT (SEQ ID NO: 16) |
| Sumo-F | CTTTAAGAAGGAGATATACCATGGCGGACTCAGAAGTCAATCTT (SEQ ID NO: 17) |
| Sumo-trF6H-F | GAGAACAGATTGGTGGTATGCCGAAGAAAAGCTCTT (SEQ ID NO: 18) |
| Sumo-trF6H-R | AAGAGCTTTTCTTCGGCATACCACCAATCTGTTCTC (SEQ ID NO: 19) |

Example 3. Construction of Recombinant Plasmids Expressing PAL, 4CL, CHS, CHI and FNSI

*Rhodotorula toruloides* PAL (GenBankAccess No. AAA33883.1), *Petroselium crispum* 4CL (GenBank Access No. KF765780.1), *Petunia* X hybrid CHS (GenBankAccess No. KF765781.1), *Medicago sativa* CHI gene (GenBankAccess No. KF765782.1), *Petroselium crispum* FNS I gene (Swiss-ProtAccess No. Q7XZQ8.1) were synthesized by GenScript and constructed into pET28a, forming plasmids pET28-PAL, pET28-4CL, pET28-CHS, pET28a-CHI, and pET28a-FNSI, respectively.

The primers in Table 2 were synthesized. PCR amplification was conducted using pET28-4CL as templates and 4CL-F-NcoI/4CL-R-BamHI as primers. pYH40 was constructed by ligation of the amplified products with NcoI/BamHI digested pCDFDuet-1.

PCR amplification was conducted using pET28-CHS as templates and CHS-F-NdeI/CHS-R-XhoI as primers. pYH50 was constructed by ligation of the amplified products with NdeI/XhoI digested pYH40.

PCR amplification was conducted using pET28a-CHI as templates and T7CHI-F-XhoI/CHI-R-AvrII as primers. Then pYH51 was constructed by ligation of the amplified products with pYH50.

PCR amplification was conducted using pET28-PAL as templates and T7PAL-F-BamH I/PAL-R-Hind III as primers. The amplified products were digested by BamH I and Hind III, and ligated with pYH51 digested by the same enzymes to form plasmid pYH55.

Figure 4:
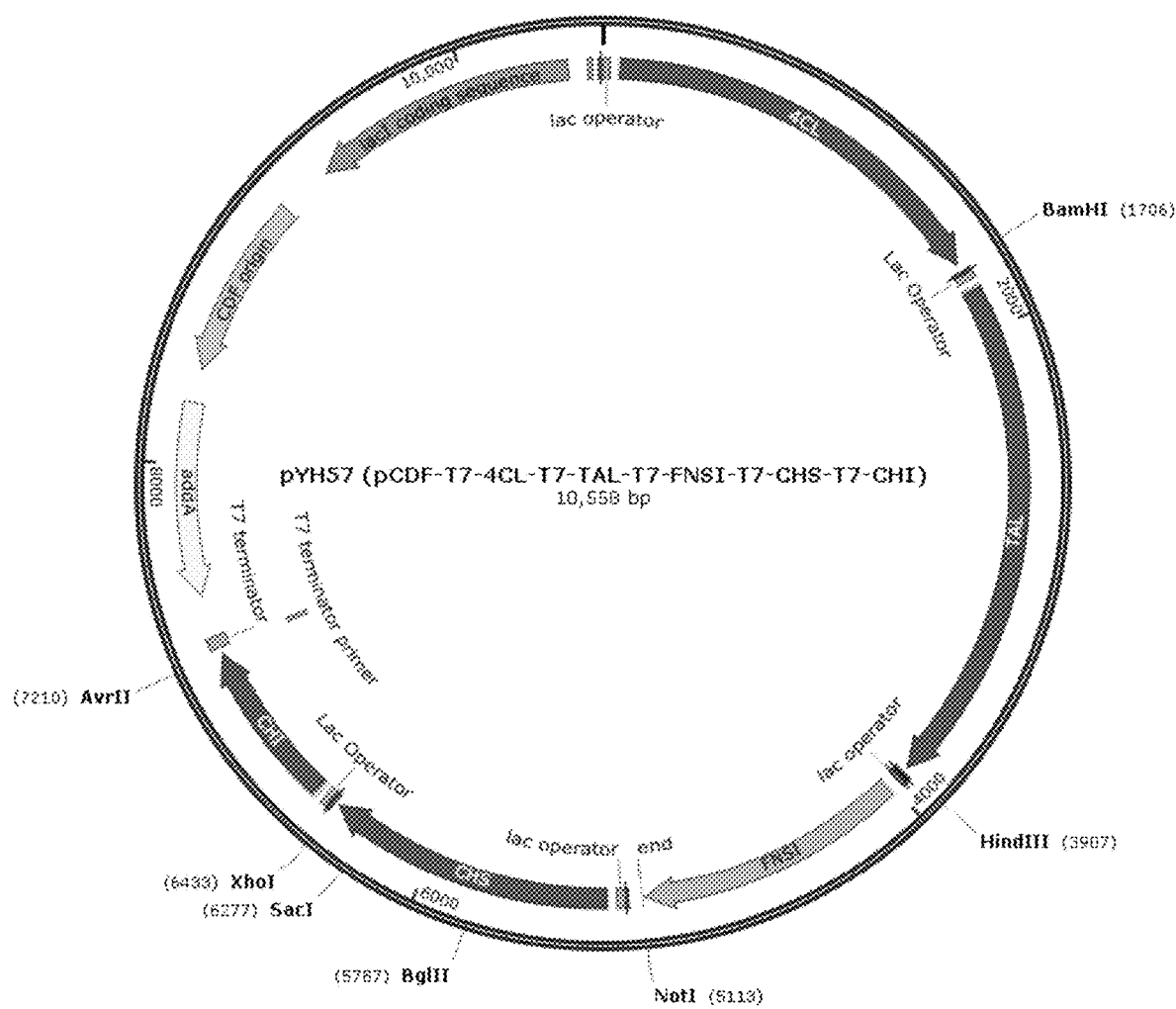
FIG. 4. Schematic of plasmid pYH57.

PCR amplification was conducted using pET28a-FNSI as templates and FNSI-HindIII-F/FNSI-NotI-R as primers. The amplified products were digested by Hind III and Not I, and ligated with pYH55 digested by the same enzymes to form plasmid pYH57. Schematic of plasmid pYH57 is shown in FIG. 4.

TABLE 2

| Primers | Sequences |
|---|---|
| 4CL-F-NcoI | TATACCATGGGTGACTGCGTTGCCCCG (SEQ ID NO: 20) |
| 4CL-R-BamHI | CGGGATCCTTACTTCGGCAGGTCGCCGCTC (SEQ ID NO: 21) |
| T7PAL-F-BamHI | CGGGATCCCTTATGCGACTCCTGCATTAG (SEQ ID NO: 22) |
| PAL-R-HindIII | GCCCAAGCTTTTATGCCAGCATCTTC (SEQ ID NO: 23) |
| CHS-F-NdeI | AGATATACATATGGTTACGGTGGAAGAATAC (SEQ ID NO: 24) |
| CHS-R-XhoI | CCGCTCGAGTTAGGTAGCCACACTATGCAG (SEQ ID NO: 25) |
| T7CHI-F-XhoI | CCGCTCGAGCTAGAAATAATTTTGTTTAAC (SEQ ID NO: 26) |
| CHI-R-AvrII | GAGCCTAGGTTAGTTACCGATTTTAAAG (SEQ ID NO: 27) |

TABLE 2-continued

| Primers | Sequences |
|---|---|
| FNSI-HindIII-F | GAAGATGCTGGCATAAAAGCTTCGATCCCGCGAAATTA (SEQ ID NO: 28) |
| FNSI-NotI-R | CGACTTAAGCATTATGCGGCCGCCTACGCCAGGTTTTC (SEQ ID NO: 29) |

Example 4. Construction and Functional Verification of Baicalein and Scutellarein Synthesizing Strains The biosynthesis process of baicalein and scutellarein is shown in FIG. 1.

The engineering strain BL21(DE3)-pYH57-pYH66 was obtained by co-transformation of the recombinant plasmids pYH66 and pYH57 into *E. coli* BL21 (DE3) competent cells.

The cells were cultured in LB solid medium (containing 80 μg/ml spectinomycin, 100 μg/ml ampicillin) overnight at 37° C. Single colony was transferred to a 2 mL LB liquid medium (containing 80 μg/ml spectinomycin, and 100 μg/ml ampicillin) and incubated overnight. The bacterial fluid was transferred to a new 10 ml MOPS liquid medium with antibiotics and incubated at 37° C. and 250 r/min until $OD_{600}$ reached 0.5-0.6. The culture was cooled down to 16° C. in a water bath. Then inducer IPTG was added at a final concentration of 1 mM, and different concentrations of sterilized phenylalanine or tyrosine was added. The mixture was placed at 22° C. for low temperature induction, and cultured for 48 h at 220 r/min. The BL21 (DE3) recombinant strain containing empty plasmid pETDuet-1 and pCDF-Duet-1 without foreign gene(s) was used as blank control, and the culture procedure was the same as above.

At the same time, the recombinant plasmids listed in Table 2 were transformed into *E. coli* and cultured to detect the production of their products.

After culture, the expression of compounds in each recombinant strain harboring recombinant plasmid was detected, which are shown in Table 3.

Figure 5:
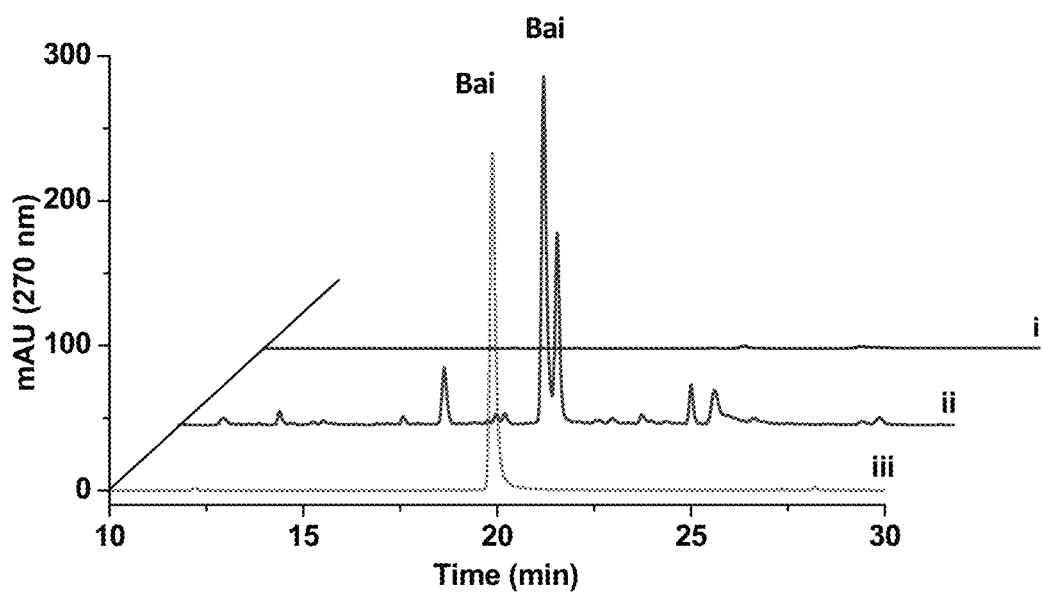
FIG. 5. HPLC results of engineering strain BL21(DE3)-pYH57-pYH66 and baicalein standard. i: BL21(DE3)-pETDuet-1-pCDFDuet-1 fermentation broth, as blank control; ii: BL21(DE3)-pYH57-pYH66 fermentation broth added with phenylalanine; baicalein standard.
Figure 6:
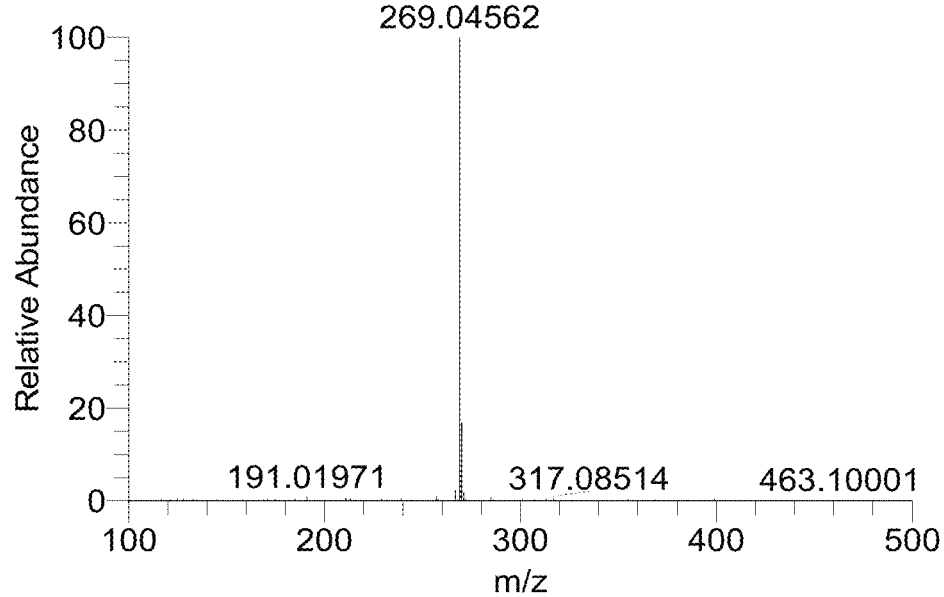
FIG. 6. Mass spectrum results of baicalein produced by engineering strain BL21(DE3)-pYH57-pYH66.

HPLC results of engineering strain BL21(DE3)-pYH57-pYH66 and baicalein standard are shown in FIG. 5. Mass spectrum results of baicalein produced by engineering strain BL21(DE3)-pYH57-pYH66 are shown in FIG. 6.

Figure 7:
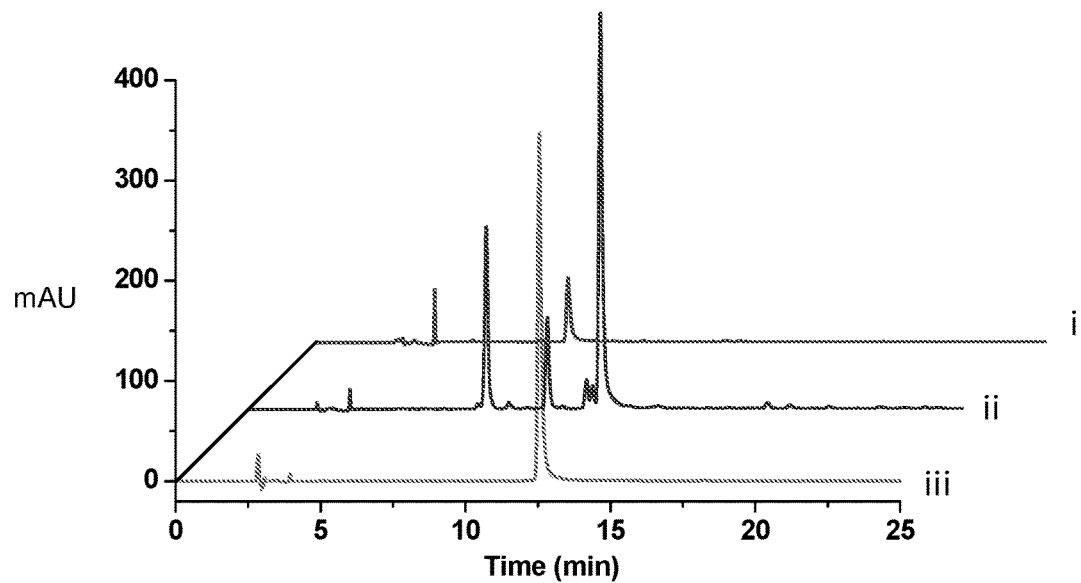
FIG. 7. HPLC results of engineering strain BL21(DE3)-pYH57-pYH66 and scutellarein standard. i: BL21(DE3)-pETDuet-1-pCDFDuet-1 fermentation broth, as blank control; ii: BL21(DE3)-pYH57-pYH66 fermentation broth added with tyrosine; iii: scutellarein standard.
Figure 8:
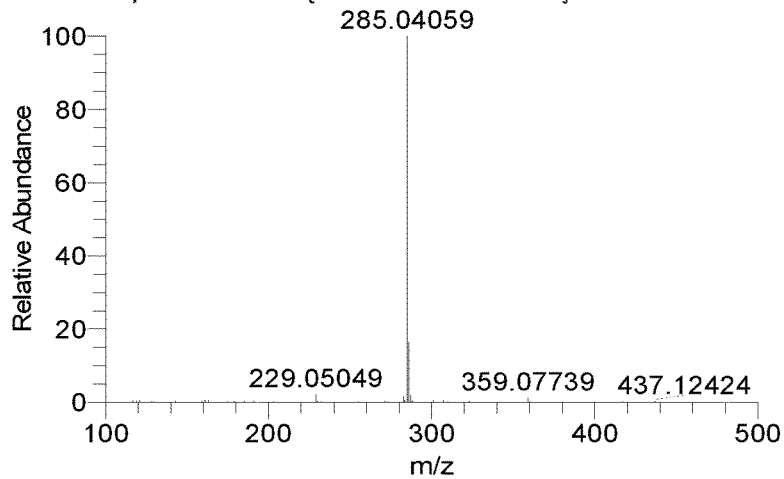
FIG. 8. Mass spectrum results of scutellarein produced by engineering strain BL21(DE3)-pYH57-pYH66.

HPLC results of engineering strain BL21(DE3)-pYH57-pYH66 and scutellarein standard are shown in FIG. 7. Mass spectrum results of scutellarein produced by engineering strain BL21(DE3)-pYH57-pYH66 are shown in FIG. 8.

Example 5: Production with Chrysin as Substrate

Six recombinant plasmids (pYH58 to pYH66) were transformed into competent cells of *E. coli* BL21 (DE3) to obtain the engineering strains BL21(DE3)-pYH58 to BL21(DE3)-pYH66, respectively.

The cells were cultured in LB solid medium (containing 100 μg/ml ampicillin) overnight at 37° C. Single colony was transferred to a 2 mL LB liquid medium (containing 100 μg/ml ampicillin) and incubated overnight. The bacterial fluid was transferred to a new 20 ml MOPS liquid medium with antibiotics and incubated at 37° C. and 250 r/min until $OD_{600}$ reached 0.5-0.6. The culture was cooled down to 16° C. in a water bath. Then inducer IPTG was added at a final concentration of 1 mM. The mixture was cultured for 12 h at 22° C. and 220 r/min. After centrifugation at 6000 rpm, 4° C. for 10 min, the supernatant was removed, and the bacteria were collected and re-suspended in a reaction buffer (50 mM Tris-HCl, pH 7.4, 0.1% Trixton) until $OD_{600}$ reached 30.5 μL chrysin (25 mM) and 2.5 μL NADPH (100 mM) were added to 1 mL of the suspension of the recombinant bacteria, and the reaction was continued at 37° C. for 8 hours. After completion of the reaction, the solution was extracted for 3 times by 10 μL HCl (6 M) and 1 mL ethyl acetate. The

TABLE 3

| Plasmids | Features | Uses |
|---|---|---|
| pYH40 | expressing 4CL protein | Synthesis of pinocembrin and naringenin |
| pYH50 | expressing 4CL and CHS proteins | |
| pYH51 | expressing 4CL, CHS and CHI proteins | |
| pYH55 | expressing PAL, 4CL, CHS and CHI proteins | |
| pYH57 | expressing PAL, 4CL, CHS, CHI and FNSI proteins | Synthesis of chrysin from phenylalanine<br>Synthesis of apigenin from tyrosine |
| pYH58 | expressing trF6H and trCPR proteins | Synthesis of baicalein from chrysin |
| pYH59 | expressing F6H and CPR proteins | Synthesis of scutellarein from apigenin |
| pYH60 | expressing 8RPF6H and trCPR proteins | |
| pYH61 | expressing SumotrF6H and trCPR proteins | |
| pYH62 | expressing MBPtrF6H and trCPR proteins | |
| pYH63 | expressing 2B1trF6H and trCPR proteins | |
| pYH64 | expressing trF6H and CPR proteins | |
| pYH65 | expressing MBPtrF6H and CPR proteins | |
| pYH66 | expressing 2B1trF6H and CPR proteins | |

It was verified that each recombinant strain of the disclosure can successfully synthesize the target compound.

HPLC results of engineering strain BL21(DE3)-pYH57-pYH66 and baicalein standard are shown in FIG. 5. Mass organic phase was concentrated, and the resulting residue was dissolved with 200 μL methanol, wherein 10 μL was used for HPLC analysis.

The conversion rates of baicalein from chrysin in each recombinant *E. coli* were shown in FIG. 9B.

HPLC results of the catalytic reaction solution of each recombinant E. coli were shown in FIG. 9C.

Each reference provided herein is incorporated by reference to the same extent as if each reference was individually incorporated by reference. In addition, it should be understood that based on the above teaching content of the disclosure, those skilled in the art can practice various changes or modifications to the disclosure, and these equivalent forms also fall within the scope of the appended claims.

We claim:

1. A method of producing baicalein and scutellarein, comprising:

(1) introducing genes expressing flavone 6-hydroxylase and cytochrome P450 oxidoreductase into a host cell to obtain a recombinant strain, wherein said flavone 6-hydroxylase is a mutant flavone 6-hydroxylase with the N-terminal amino acids 2 to 25 truncated and fused with a peptide tag, said peptide tag is a 2B1 family soluble protein of cytochrome P450, and said host cell is a *Escherichia coli* cell;

(2) culturing the recombinant host cell in a culture system containing chrysin or apigenin to produce baicalein or scutellarein.

2. A method of producing baicalein and scutellarein, comprising:
   (1) introducing genes expressing flavone 6-hydroxylase and cytochrome P450 oxidoreductase, as well as genes for synthesizing chrysin or apigenin, into a host cell, wherein said flavone 6-hydroxylase is a mutant flavone 6-hydroxylase with the N-terminal amino acids 2 to 25 truncated and fused with a peptide tag, said peptide tag is a 2B1 family soluble protein of cytochrome P450, and said host cell is a *Escherichia coli* cell;
   (2) culturing the host cell in a culture system containing phenylalanine and/or tyrosine to produce baicalein or scutellarein.

3. The method according to claim 2, wherein, the genes for synthesizing chrysin or apigenin comprises: genes expressing phenylalanine ammonia-lyase, 4-coumarate: CoA ligase, chalcone synthase, chalcone isomerase and flavone synthase I.

4. The method according to claim 3, wherein, when introduced into the host cell, the genes expressing phenylalanine ammonia-lyase, 4-coumarate: CoA ligase, chalcone synthase, chalcone isomerase and flavone synthase I are in the same expression vector.

5. The method according to claim 2, wherein, the cytochrome P450 oxidoreductase is a full-length or mutant cytochrome P450 oxidoreductase with the N-terminal amino acids (1-20) to (60-85) truncated.

6. The method according to claim 2, wherein, the cytochrome P450 oxidoreductase is a full-length or mutant cytochrome P450 oxidoreductase with the N-terminal amino acids (2-10) to (65-80) truncated.

7. The method according to claim 2, wherein, the cytochrome P450 oxidoreductase is a full-length or mutant cytochrome P450 oxidoreductase with the N-terminal amino acids (2-5) to (70-75) truncated.

* * * * *

```
                        SEQUENCE LISTING

<160> NUMBER OF SEQ ID NOS: 29

<210> SEQ ID NO 1
<211> LENGTH: 517
<212> TYPE: PRT
<213> ORGANISM: Scutellaria baicalensis

<400> SEQUENCE: 1

Met Glu Leu Ser Ser Val Ile Tyr Gly Ala Ile Ala Leu Leu Ser Leu
1               5                   10                  15

Phe Tyr Cys Tyr Leu His Phe Ser Lys Pro Lys Lys Ser Ser Leu Asn
                20                  25                  30

Ala Pro Pro Glu Ala Gly Gly Ala Arg Phe Ile Thr Gly His Leu His
            35                  40                  45

Leu Met Asp Gly Arg Ser Ala Ser Asp Lys Leu Pro His Ile Asn Leu
    50                  55                      60

Gly Leu Leu Ala Asp Gln His Gly Pro Ile Phe Thr Ile Arg Leu Gly
65                  70                  75                  80

Val His Arg Ala Val Val Ser Ser Trp Glu Leu Ala Lys Glu Ile
                85                  90                  95

Phe Thr Thr His Asp Thr Ala Val Met Ala Arg Pro Arg Leu Ile Ala
                100                 105                 110

Asp Asp Tyr Leu Ser Tyr Asp Gly Ala Ser Leu Gly Phe Ser Pro Tyr
            115                 120                 125

Gly Pro Tyr Trp Arg Glu Ile Arg Lys Leu Val Thr Thr Glu Leu Leu
    130                 135                 140

Ser Ala Arg Arg Ile Glu Leu Gln Arg Ala Thr Arg Val Arg Glu Ile
145                 150                 155                 160

Thr Gln Phe Thr Gly Glu Leu Tyr Lys Leu Trp Glu Glu Lys Lys Asp
                165                 170                 175

Gly Ser Gly Arg Val Leu Val Asp Met Lys Gln Trp Leu Gly Asn Leu
            180                 185                 190

Ser Leu Asn Leu Val Ser Arg Met Val Val Gly Lys Arg Phe Tyr Gly
    195                 200                 205

Gly Asp Asp Ser Glu Thr Thr Lys Arg Trp Arg Gly Val Met Arg Glu
210                 215                 220

Phe Phe Gln Leu Ile Gly Gln Phe Ile Pro Gly Asp Gly Leu Pro Phe
225                 230                 235                 240

Leu Arg Trp Leu Asp Leu Gly Gly Phe Glu Lys Arg Thr Arg Asp Thr
                245                 250                 255

Ala Tyr Glu Leu Asp Lys Ile Ile Ala Met Trp Leu Ala Glu Tyr Arg
            260                 265                 270

Lys Arg Glu Tyr Ser Gly Asp Asp Lys Glu Gln Cys Phe Met Ala Leu
    275                 280                 285

Met Leu Ser Leu Val Gln Ala Asn Pro Thr Leu Gln Leu His Tyr Asp
        290                 295                 300

Ala Asp Thr Ile Ile Lys Ala Thr Cys Gln Val Leu Ile Ser Ala Ala
305                 310                 315                 320

Ser Asp Thr Thr Thr Val Ile Leu Ile Trp Val Ile Ser Leu Leu Leu
                325                 330                 335
```

```
Asn Asn Ala Asp Val Leu Lys Lys Val Gln Glu Leu Asp Glu Gln
            340                 345                 350

Val Gly Arg Glu Arg Val Glu Glu Ser Asp Ile Ser Asn Leu Pro
            355                 360                 365

Tyr Leu Gln Ala Val Val Lys Glu Thr Met Arg Leu Tyr Pro Pro Ala
            370                 375                 380

Pro Phe Ala Gly Val Arg Ala Phe Ser Glu Asp Cys Thr Val Gly Gly
385                 390                 395                 400

Tyr His Ile Gln Lys Gly Thr Phe Leu Ile Val Asn Leu Trp Lys Leu
            405                 410                 415

His Arg Asp Pro Arg Val Trp Ser Asp Asp Ala Leu Glu Phe Lys Pro
            420                 425                 430

Gln Arg Phe Phe Asp Lys Lys Val Glu Val Lys Gly Gln Asp Phe Glu
            435                 440                 445

Leu Met Pro Phe Gly Gly Arg Arg Met Cys Pro Gly Ser Asn Leu
            450                 455                 460

Gly Met His Met Val His Phe Val Leu Ala Asn Ile Leu Gln Ala Phe
465                 470                 475                 480

Asp Ile Thr Thr Gly Ser Thr Val Asp Met Thr Glu Ser Val Gly Leu
            485                 490                 495

Thr Asn Met Lys Ala Thr Pro Leu Asp Ala Ile Leu Thr Pro Arg Leu
            500                 505                 510

Ser Pro Thr Leu Tyr
            515

<210> SEQ ID NO 2
<211> LENGTH: 495
<212> TYPE: PRT
<213> ORGANISM: Artificial Sequence
<220> FEATURE:
<223> OTHER INFORMATION: F6H mutant

<400> SEQUENCE: 2

Met Ala Met Pro Lys Lys Ser Ser Leu Asn Ala Pro Pro Glu Ala Gly
1               5                   10                  15

Gly Ala Arg Phe Ile Thr Gly His Leu His Leu Met Asp Gly Arg Ser
            20                  25                  30

Ala Ser Asp Lys Leu Pro His Ile Asn Leu Gly Leu Leu Ala Asp Gln
            35                  40                  45

His Gly Pro Ile Phe Thr Ile Arg Leu Gly Val His Arg Ala Val Val
        50                  55                  60

Val Ser Ser Trp Glu Leu Ala Lys Glu Ile Phe Thr Thr His Asp Thr
65              70                  75                  80

Ala Val Met Ala Arg Pro Arg Leu Ile Ala Asp Asp Tyr Leu Ser Tyr
            85                  90                  95

Asp Gly Ala Ser Leu Gly Phe Ser Pro Tyr Gly Pro Tyr Trp Arg Glu
            100                 105                 110

Ile Arg Lys Leu Val Thr Thr Glu Leu Leu Ser Ala Arg Arg Ile Glu
            115                 120                 125

Leu Gln Arg Ala Thr Arg Val Arg Glu Ile Thr Gln Phe Thr Gly Glu
            130                 135                 140

Leu Tyr Lys Leu Trp Glu Glu Lys Lys Asp Gly Ser Gly Arg Val Leu
145                 150                 155                 160

Val Asp Met Lys Gln Trp Leu Gly Asn Leu Ser Leu Asn Leu Val Ser
            165                 170                 175
```

```
Arg Met Val Val Gly Lys Arg Phe Tyr Gly Gly Asp Ser Glu Thr
            180                 185                 190

Thr Lys Arg Trp Arg Gly Val Met Arg Glu Phe Phe Gln Leu Ile Gly
        195                 200                 205

Gln Phe Ile Pro Gly Asp Gly Leu Pro Phe Leu Arg Trp Leu Asp Leu
    210                 215                 220

Gly Gly Phe Glu Lys Arg Thr Arg Asp Thr Ala Tyr Glu Leu Asp Lys
225                 230                 235                 240

Ile Ile Ala Met Trp Leu Ala Glu Tyr Arg Lys Arg Glu Tyr Ser Gly
                245                 250                 255

Asp Asp Lys Glu Gln Cys Phe Met Ala Leu Met Leu Ser Leu Val Gln
            260                 265                 270

Ala Asn Pro Thr Leu Gln Leu His Tyr Asp Ala Asp Thr Ile Ile Lys
            275                 280                 285

Ala Thr Cys Gln Val Leu Ile Ser Ala Ala Ser Asp Thr Thr Thr Val
            290                 295                 300

Ile Leu Ile Trp Val Ile Ser Leu Leu Leu Asn Asn Ala Asp Val Leu
305                 310                 315                 320

Lys Lys Val Gln Glu Glu Leu Asp Glu Gln Val Gly Arg Glu Arg Arg
                325                 330                 335

Val Glu Glu Ser Asp Ile Ser Asn Leu Pro Tyr Leu Gln Ala Val Val
            340                 345                 350

Lys Glu Thr Met Arg Leu Tyr Pro Pro Ala Pro Phe Ala Gly Val Arg
            355                 360                 365

Ala Phe Ser Glu Asp Cys Thr Val Gly Gly Tyr His Ile Gln Lys Gly
            370                 375                 380

Thr Phe Leu Ile Val Asn Leu Trp Lys Leu His Arg Asp Pro Arg Val
385                 390                 395                 400

Trp Ser Asp Asp Ala Leu Glu Phe Lys Pro Gln Arg Phe Phe Asp Lys
                405                 410                 415

Lys Val Glu Val Lys Gly Gln Asp Phe Glu Leu Met Pro Phe Gly Gly
            420                 425                 430

Gly Arg Arg Met Cys Pro Gly Ser Asn Leu Gly Met His Met Val His
            435                 440                 445

Phe Val Leu Ala Asn Ile Leu Gln Ala Phe Asp Ile Thr Thr Gly Ser
            450                 455                 460

Thr Val Asp Met Thr Glu Ser Val Gly Leu Thr Asn Met Lys Ala Thr
465                 470                 475                 480

Pro Leu Asp Ala Ile Leu Thr Pro Arg Leu Ser Pro Thr Leu Tyr
                485                 490                 495

<210> SEQ ID NO 3
<211> LENGTH: 501
<212> TYPE: PRT
<213> ORGANISM: Artificial Sequence
<220> FEATURE:
<223> OTHER INFORMATION: F6H mutant 8RPtrF6H

<400> SEQUENCE: 3

Met Ala Leu Leu Leu Ala Val Phe Met Pro Lys Lys Ser Ser Leu Asn
1               5                   10                  15

Ala Pro Pro Glu Ala Gly Gly Ala Arg Phe Ile Thr Gly His Leu His
            20                  25                  30

Leu Met Asp Gly Arg Ser Ala Ser Asp Lys Leu Pro His Ile Asn Leu
        35                  40                  45
```

```
Gly Leu Leu Ala Asp Gln His Gly Pro Ile Phe Thr Ile Arg Leu Gly
         50                  55                  60

Val His Arg Ala Val Val Ser Ser Trp Glu Leu Ala Lys Glu Ile
65                  70                  75                  80

Phe Thr Thr His Asp Thr Ala Val Met Ala Arg Pro Arg Leu Ile Ala
                    85                  90                  95

Asp Asp Tyr Leu Ser Tyr Asp Gly Ala Ser Leu Gly Phe Ser Pro Tyr
                100                 105                 110

Gly Pro Tyr Trp Arg Glu Ile Arg Lys Leu Val Thr Thr Glu Leu Leu
                115                 120                 125

Ser Ala Arg Arg Ile Glu Leu Gln Arg Ala Thr Arg Val Arg Glu Ile
        130                 135                 140

Thr Gln Phe Thr Gly Glu Leu Tyr Lys Leu Trp Glu Glu Lys Lys Asp
145                 150                 155                 160

Gly Ser Gly Arg Val Leu Val Asp Met Lys Gln Trp Leu Gly Asn Leu
                165                 170                 175

Ser Leu Asn Leu Val Ser Arg Met Val Val Gly Lys Arg Phe Tyr Gly
            180                 185                 190

Gly Asp Asp Ser Glu Thr Thr Lys Arg Trp Arg Gly Val Met Arg Glu
        195                 200                 205

Phe Phe Gln Leu Ile Gly Gln Phe Ile Pro Gly Asp Gly Leu Pro Phe
210                 215                 220

Leu Arg Trp Leu Asp Leu Gly Gly Phe Glu Lys Arg Thr Arg Asp Thr
225                 230                 235                 240

Ala Tyr Glu Leu Asp Lys Ile Ile Ala Met Trp Leu Ala Glu Tyr Arg
                245                 250                 255

Lys Arg Glu Tyr Ser Gly Asp Asp Lys Glu Gln Cys Phe Met Ala Leu
                260                 265                 270

Met Leu Ser Leu Val Gln Ala Asn Pro Thr Leu Gln Leu His Tyr Asp
        275                 280                 285

Ala Asp Thr Ile Ile Lys Ala Thr Cys Gln Val Leu Ile Ser Ala Ala
        290                 295                 300

Ser Asp Thr Thr Thr Val Ile Leu Ile Trp Val Ile Ser Leu Leu Leu
305                 310                 315                 320

Asn Asn Ala Asp Val Leu Lys Lys Val Gln Glu Glu Leu Asp Glu Gln
                325                 330                 335

Val Gly Arg Glu Arg Val Glu Glu Ser Asp Ile Ser Asn Leu Pro
                340                 345                 350

Tyr Leu Gln Ala Val Lys Glu Thr Met Arg Leu Tyr Pro Pro Ala
        355                 360                 365

Pro Phe Ala Gly Val Arg Ala Phe Ser Glu Asp Cys Thr Val Gly Gly
        370                 375                 380

Tyr His Ile Gln Lys Gly Thr Phe Leu Ile Val Asn Leu Trp Lys Leu
385                 390                 395                 400

His Arg Asp Pro Arg Val Trp Ser Asp Asp Ala Leu Glu Phe Lys Pro
                405                 410                 415

Gln Arg Phe Phe Asp Lys Lys Val Glu Val Lys Gly Gln Asp Phe Glu
                420                 425                 430

Leu Met Pro Phe Gly Gly Gly Arg Arg Met Cys Pro Gly Ser Asn Leu
        435                 440                 445

Gly Met His Met Val His Phe Val Leu Ala Asn Ile Leu Gln Ala Phe
        450                 455                 460
```

```
Asp Ile Thr Thr Gly Ser Thr Val Asp Met Thr Glu Ser Val Gly Leu
465                 470                 475                 480

Thr Asn Met Lys Ala Thr Pro Leu Asp Ala Ile Leu Thr Pro Arg Leu
                485                 490                 495

Ser Pro Thr Leu Tyr
            500

<210> SEQ ID NO 4
<211> LENGTH: 591
<212> TYPE: PRT
<213> ORGANISM: Artificial Sequence
<220> FEATURE:
<223> OTHER INFORMATION: F6H mutant SumotrF6H

<400> SEQUENCE: 4

Met Ala Asp Ser Glu Val Asn Gln Glu Ala Lys Pro Glu Val Lys Pro
1               5                   10                  15

Glu Val Lys Pro Glu Thr His Ile Asn Leu Lys Val Ser Asp Gly Ser
                20                  25                  30

Ser Glu Ile Phe Phe Lys Ile Lys Lys Thr Thr Pro Leu Arg Arg Leu
            35                  40                  45

Met Glu Ala Phe Ala Lys Arg Gln Gly Lys Glu Met Asp Ser Leu Arg
50                  55                  60

Phe Leu Tyr Asp Gly Ile Arg Ile Gln Ala Asp Gln Thr Pro Glu Asp
65                  70                  75                  80

Leu Asp Met Glu Asp Asn Asp Ile Ile Glu Ala His Arg Glu Gln Ile
                85                  90                  95

Gly Gly Met Pro Lys Lys Ser Ser Leu Asn Ala Pro Pro Glu Ala Gly
                100                 105                 110

Gly Ala Arg Phe Ile Thr Gly His Leu His Leu Met Asp Gly Arg Ser
            115                 120                 125

Ala Ser Asp Lys Leu Pro His Ile Asn Leu Gly Leu Leu Ala Asp Gln
130                 135                 140

His Gly Pro Ile Phe Thr Ile Arg Leu Gly Val His Arg Ala Val Val
145                 150                 155                 160

Val Ser Ser Trp Glu Leu Ala Lys Glu Ile Phe Thr Thr His Asp Thr
                165                 170                 175

Ala Val Met Ala Arg Pro Arg Leu Ile Ala Asp Asp Tyr Leu Ser Tyr
            180                 185                 190

Asp Gly Ala Ser Leu Gly Phe Ser Pro Tyr Gly Pro Tyr Trp Arg Glu
        195                 200                 205

Ile Arg Lys Leu Val Thr Thr Glu Leu Leu Ser Ala Arg Ile Glu
210                 215                 220

Leu Gln Arg Ala Thr Arg Val Arg Glu Ile Thr Gln Phe Thr Gly Glu
225                 230                 235                 240

Leu Tyr Lys Leu Trp Glu Glu Lys Lys Asp Gly Ser Gly Arg Val Leu
                245                 250                 255

Val Asp Met Lys Gln Trp Leu Gly Asn Leu Ser Leu Asn Leu Val Ser
            260                 265                 270

Arg Met Val Val Gly Lys Arg Phe Tyr Gly Gly Asp Asp Ser Glu Thr
        275                 280                 285

Thr Lys Arg Trp Arg Gly Val Met Arg Glu Phe Phe Gln Leu Ile Gly
    290                 295                 300

Gln Phe Ile Pro Gly Asp Gly Leu Pro Phe Leu Arg Trp Leu Asp Leu
305                 310                 315                 320
```

Gly Gly Phe Glu Lys Arg Thr Arg Asp Thr Ala Tyr Glu Leu Asp Lys
                    325                 330                 335

Ile Ile Ala Met Trp Leu Ala Glu Tyr Arg Lys Arg Glu Tyr Ser Gly
            340                 345                 350

Asp Asp Lys Glu Gln Cys Phe Met Ala Leu Met Leu Ser Leu Val Gln
            355                 360                 365

Ala Asn Pro Thr Leu Gln Leu His Tyr Asp Ala Asp Thr Ile Ile Lys
            370                 375                 380

Ala Thr Cys Gln Val Leu Ile Ser Ala Ala Ser Asp Thr Thr Thr Val
385                 390                 395                 400

Ile Leu Ile Trp Val Ile Ser Leu Leu Leu Asn Asn Ala Asp Val Leu
                405                 410                 415

Lys Lys Val Gln Glu Glu Leu Asp Glu Gln Val Gly Arg Glu Arg Arg
                420                 425                 430

Val Glu Glu Ser Asp Ile Ser Asn Leu Pro Tyr Leu Gln Ala Val Val
                435                 440                 445

Lys Glu Thr Met Arg Leu Tyr Pro Pro Ala Pro Phe Ala Gly Val Arg
                450                 455                 460

Ala Phe Ser Glu Asp Cys Thr Val Gly Gly Tyr His Ile Gln Lys Gly
465                 470                 475                 480

Thr Phe Leu Ile Val Asn Leu Trp Lys Leu His Arg Asp Pro Arg Val
                485                 490                 495

Trp Ser Asp Asp Ala Leu Glu Phe Lys Pro Gln Arg Phe Phe Asp Lys
                500                 505                 510

Lys Val Glu Val Lys Gly Gln Asp Phe Glu Leu Met Pro Phe Gly Gly
                515                 520                 525

Gly Arg Arg Met Cys Pro Gly Ser Asn Leu Gly Met His Met Val His
                530                 535                 540

Phe Val Leu Ala Asn Ile Leu Gln Ala Phe Asp Ile Thr Thr Gly Ser
545                 550                 555                 560

Thr Val Asp Met Thr Glu Ser Val Gly Leu Thr Asn Met Lys Ala Thr
                565                 570                 575

Pro Leu Asp Ala Ile Leu Thr Pro Arg Leu Ser Pro Thr Leu Tyr
                580                 585                 590

<210> SEQ ID NO 5
<211> LENGTH: 861
<212> TYPE: PRT
<213> ORGANISM: Artificial Sequence
<220> FEATURE:
<223> OTHER INFORMATION: F6H mutant MBPtrF6H

<400> SEQUENCE: 5

Met Ala Lys Ile Glu Glu Gly Lys Leu Val Ile Trp Ile Asn Gly Asp
1               5                   10                  15

Lys Gly Tyr Asn Gly Leu Ala Glu Val Gly Lys Lys Phe Glu Lys Asp
                20                  25                  30

Thr Gly Ile Lys Val Thr Val Glu His Pro Asp Lys Leu Glu Glu Lys
            35                  40                  45

Phe Pro Gln Val Ala Ala Thr Gly Asp Gly Pro Asp Ile Ile Phe Trp
        50                  55                  60

Ala His Asp Arg Phe Gly Gly Tyr Ala Gln Ser Gly Leu Leu Ala Glu
65                  70                  75                  80

Ile Thr Pro Asp Lys Ala Phe Gln Asp Lys Leu Tyr Pro Phe Thr Trp
                85                  90                  95

```
Asp Ala Val Arg Tyr Asn Gly Lys Leu Ile Ala Tyr Pro Ile Ala Val
            100                 105                 110
Glu Ala Leu Ser Leu Ile Tyr Asn Lys Asp Leu Leu Pro Asn Pro Pro
        115                 120                 125
Lys Thr Trp Glu Glu Ile Pro Ala Leu Asp Lys Glu Leu Lys Ala Lys
    130                 135                 140
Gly Lys Ser Ala Leu Met Phe Asn Leu Gln Glu Pro Tyr Phe Thr Trp
145                 150                 155                 160
Pro Leu Ile Ala Ala Asp Gly Gly Tyr Ala Phe Lys Tyr Glu Asn Gly
                165                 170                 175
Lys Tyr Asp Ile Lys Asp Val Gly Val Asp Asn Ala Gly Ala Lys Ala
            180                 185                 190
Gly Leu Thr Phe Leu Val Asp Leu Ile Lys Asn Lys His Met Asn Ala
        195                 200                 205
Asp Thr Asp Tyr Ser Ile Ala Glu Ala Ala Phe Asn Lys Gly Glu Thr
    210                 215                 220
Ala Met Thr Ile Asn Gly Pro Trp Ala Trp Ser Asn Ile Asp Thr Ser
225                 230                 235                 240
Lys Val Asn Tyr Gly Val Thr Val Leu Pro Thr Phe Lys Gly Gln Pro
                245                 250                 255
Ser Lys Pro Phe Val Gly Val Leu Ser Ala Gly Ile Asn Ala Ala Ser
            260                 265                 270
Pro Asn Lys Glu Leu Ala Lys Glu Phe Leu Glu Asn Tyr Leu Leu Thr
        275                 280                 285
Asp Glu Gly Leu Glu Ala Val Asn Lys Asp Lys Pro Leu Gly Ala Val
    290                 295                 300
Ala Leu Lys Ser Tyr Glu Glu Glu Leu Val Lys Asp Pro Arg Ile Ala
305                 310                 315                 320
Ala Thr Met Glu Asn Ala Gln Lys Gly Glu Ile Met Pro Asn Ile Pro
                325                 330                 335
Gln Met Ser Ala Phe Trp Tyr Ala Val Arg Thr Ala Val Ile Asn Ala
            340                 345                 350
Ala Ser Gly Arg Gln Thr Val Asp Glu Ala Leu Lys Asp Ala Gln Thr
        355                 360                 365
Met Pro Lys Lys Ser Ser Leu Asn Ala Pro Pro Glu Ala Gly Gly Ala
    370                 375                 380
Arg Phe Ile Thr Gly His Leu His Leu Met Asp Gly Arg Ser Ala Ser
385                 390                 395                 400
Asp Lys Leu Pro His Ile Asn Leu Gly Leu Leu Ala Asp Gln His Gly
                405                 410                 415
Pro Ile Phe Thr Ile Arg Leu Gly Val His Arg Ala Val Val Val Ser
            420                 425                 430
Ser Trp Glu Leu Ala Lys Glu Ile Phe Thr Thr His Asp Thr Ala Val
        435                 440                 445
Met Ala Arg Pro Arg Leu Ile Ala Asp Asp Tyr Leu Ser Tyr Asp Gly
    450                 455                 460
Ala Ser Leu Gly Phe Ser Pro Tyr Gly Pro Tyr Trp Arg Glu Ile Arg
465                 470                 475                 480
Lys Leu Val Thr Thr Glu Leu Leu Ser Ala Arg Arg Ile Glu Leu Gln
                485                 490                 495
Arg Ala Thr Arg Val Arg Glu Ile Thr Gln Phe Thr Gly Glu Leu Tyr
            500                 505                 510
Lys Leu Trp Glu Glu Lys Lys Asp Gly Ser Gly Arg Val Leu Val Asp
```

```
            515                 520                 525
Met Lys Gln Trp Leu Gly Asn Leu Ser Leu Asn Leu Val Ser Arg Met
    530                 535                 540

Val Val Gly Lys Arg Phe Tyr Gly Gly Asp Asp Ser Glu Thr Thr Lys
545                 550                 555                 560

Arg Trp Arg Gly Val Met Arg Glu Phe Phe Gln Leu Ile Gly Gln Phe
                565                 570                 575

Ile Pro Gly Asp Gly Leu Pro Phe Leu Arg Trp Leu Asp Leu Gly Gly
            580                 585                 590

Phe Glu Lys Arg Thr Arg Asp Thr Ala Tyr Glu Leu Asp Lys Ile Ile
        595                 600                 605

Ala Met Trp Leu Ala Glu Tyr Arg Lys Arg Glu Tyr Ser Gly Asp Asp
    610                 615                 620

Lys Glu Gln Cys Phe Met Ala Leu Met Leu Ser Leu Val Gln Ala Asn
625                 630                 635                 640

Pro Thr Leu Gln Leu His Tyr Asp Ala Asp Thr Ile Ile Lys Ala Thr
                645                 650                 655

Cys Gln Val Leu Ile Ser Ala Ala Ser Asp Thr Thr Thr Val Ile Leu
            660                 665                 670

Ile Trp Val Ile Ser Leu Leu Leu Asn Asn Ala Asp Val Leu Lys Lys
        675                 680                 685

Val Gln Glu Glu Leu Asp Glu Gln Val Gly Arg Glu Arg Val Glu
    690                 695                 700

Glu Ser Asp Ile Ser Asn Leu Pro Tyr Leu Gln Ala Val Val Lys Glu
705                 710                 715                 720

Thr Met Arg Leu Tyr Pro Pro Ala Pro Phe Ala Gly Val Arg Ala Phe
                725                 730                 735

Ser Glu Asp Cys Thr Val Gly Gly Tyr His Ile Gln Lys Gly Thr Phe
            740                 745                 750

Leu Ile Val Asn Leu Trp Lys Leu His Arg Asp Pro Arg Val Trp Ser
        755                 760                 765

Asp Asp Ala Leu Glu Phe Lys Pro Gln Arg Phe Phe Asp Lys Lys Val
    770                 775                 780

Glu Val Lys Gly Gln Asp Phe Glu Leu Met Pro Phe Gly Gly Gly Arg
785                 790                 795                 800

Arg Met Cys Pro Gly Ser Asn Leu Gly Met His Met Val His Phe Val
                805                 810                 815

Leu Ala Asn Ile Leu Gln Ala Phe Asp Ile Thr Thr Gly Ser Thr Val
            820                 825                 830

Asp Met Thr Glu Ser Val Gly Leu Thr Asn Met Lys Ala Thr Pro Leu
        835                 840                 845

Asp Ala Ile Leu Thr Pro Arg Leu Ser Pro Thr Leu Tyr
    850                 855                 860

<210> SEQ ID NO 6
<211> LENGTH: 509
<212> TYPE: PRT
<213> ORGANISM: Artificial Sequence
<220> FEATURE:
<223> OTHER INFORMATION: F6H mutant 2B1trF6H

<400> SEQUENCE: 6

Met Ala Lys Lys Thr Ser Ser Lys Gly Lys Leu Pro Pro Gly Pro Ser
1               5                   10                  15

Met Pro Lys Lys Ser Ser Leu Asn Ala Pro Pro Glu Ala Gly Gly Ala
```

```
                20                  25                  30
Arg Phe Ile Thr Gly His Leu His Leu Met Asp Gly Arg Ser Ala Ser
            35                  40                  45

Asp Lys Leu Pro His Ile Asn Leu Gly Leu Leu Ala Asp Gln His Gly
        50                  55                  60

Pro Ile Phe Thr Ile Arg Leu Gly Val His Arg Ala Val Val Val Ser
65                  70                  75                  80

Ser Trp Glu Leu Ala Lys Glu Ile Phe Thr Thr His Asp Thr Ala Val
                85                  90                  95

Met Ala Arg Pro Arg Leu Ile Ala Asp Asp Tyr Leu Ser Tyr Asp Gly
            100                 105                 110

Ala Ser Leu Gly Phe Ser Pro Tyr Gly Pro Tyr Trp Arg Glu Ile Arg
        115                 120                 125

Lys Leu Val Thr Thr Glu Leu Leu Ser Ala Arg Arg Ile Glu Leu Gln
    130                 135                 140

Arg Ala Thr Arg Val Arg Glu Ile Thr Gln Phe Thr Gly Glu Leu Tyr
145                 150                 155                 160

Lys Leu Trp Glu Glu Lys Lys Asp Gly Ser Gly Arg Val Leu Val Asp
                165                 170                 175

Met Lys Gln Trp Leu Gly Asn Leu Ser Leu Asn Leu Val Ser Arg Met
            180                 185                 190

Val Val Gly Lys Arg Phe Tyr Gly Gly Asp Asp Ser Glu Thr Thr Lys
        195                 200                 205

Arg Trp Arg Gly Val Met Arg Glu Phe Phe Gln Leu Ile Gly Gln Phe
    210                 215                 220

Ile Pro Gly Asp Gly Leu Pro Phe Leu Arg Trp Leu Asp Leu Gly Gly
225                 230                 235                 240

Phe Glu Lys Arg Thr Arg Asp Thr Ala Tyr Glu Leu Asp Lys Ile Ile
                245                 250                 255

Ala Met Trp Leu Ala Glu Tyr Arg Lys Arg Glu Tyr Ser Gly Asp Asp
            260                 265                 270

Lys Glu Gln Cys Phe Met Ala Leu Met Leu Ser Leu Val Gln Ala Asn
        275                 280                 285

Pro Thr Leu Gln Leu His Tyr Asp Ala Asp Thr Ile Ile Lys Ala Thr
    290                 295                 300

Cys Gln Val Leu Ile Ser Ala Ala Ser Asp Thr Thr Thr Val Ile Leu
305                 310                 315                 320

Ile Trp Val Ile Ser Leu Leu Leu Asn Asn Ala Asp Val Leu Lys Lys
                325                 330                 335

Val Gln Glu Glu Leu Asp Glu Gln Val Gly Arg Glu Arg Val Glu
            340                 345                 350

Glu Ser Asp Ile Ser Asn Leu Pro Tyr Leu Gln Ala Val Lys Glu
        355                 360                 365

Thr Met Arg Leu Tyr Pro Pro Ala Pro Phe Ala Gly Val Arg Ala Phe
    370                 375                 380

Ser Glu Asp Cys Thr Val Gly Gly Tyr His Ile Gln Lys Gly Thr Phe
385                 390                 395                 400

Leu Ile Val Asn Leu Trp Lys Leu His Arg Asp Pro Arg Val Trp Ser
                405                 410                 415

Asp Asp Ala Leu Glu Phe Lys Pro Gln Arg Phe Phe Asp Lys Lys Val
            420                 425                 430

Glu Val Lys Gly Gln Asp Phe Glu Leu Met Pro Phe Gly Gly Arg
        435                 440                 445
```

```
Arg Met Cys Pro Gly Ser Asn Leu Gly Met His Met His Phe Val
    450                 455                 460

Leu Ala Asn Ile Leu Gln Ala Phe Asp Ile Thr Thr Gly Ser Thr Val
465                 470                 475                 480

Asp Met Thr Glu Ser Val Gly Leu Thr Asn Met Lys Ala Thr Pro Leu
                485                 490                 495

Asp Ala Ile Leu Thr Pro Arg Leu Ser Pro Thr Leu Tyr
            500                 505

<210> SEQ ID NO 7
<211> LENGTH: 712
<212> TYPE: PRT
<213> ORGANISM: Arabidopsis thaliana

<400> SEQUENCE: 7

Met Ser Ser Ser Ser Ser Thr Ser Met Ile Asp Leu Met Ala
1               5                   10                  15

Ala Ile Ile Lys Gly Glu Pro Val Ile Val Ser Asp Pro Ala Asn Ala
            20                  25                  30

Ser Ala Tyr Glu Ser Val Ala Ala Glu Leu Ser Ser Met Leu Ile Glu
        35                  40                  45

Asn Arg Gln Phe Ala Met Ile Val Thr Thr Ser Ile Ala Val Leu Ile
    50                  55                  60

Gly Cys Ile Val Met Leu Val Trp Arg Arg Ser Gly Ser Gly Asn Ser
65                  70                  75                  80

Lys Arg Val Glu Pro Leu Lys Pro Leu Val Ile Lys Pro Arg Glu Glu
                85                  90                  95

Glu Ile Asp Asp Gly Arg Lys Lys Val Thr Ile Phe Phe Gly Thr Gln
                100                 105                 110

Thr Gly Thr Ala Glu Gly Phe Ala Lys Ala Leu Gly Glu Glu Ala Lys
            115                 120                 125

Ala Arg Tyr Glu Lys Thr Arg Phe Lys Ile Val Asp Leu Asp Asp Tyr
        130                 135                 140

Ala Ala Asp Asp Asp Glu Tyr Glu Glu Lys Leu Lys Lys Glu Asp Val
145                 150                 155                 160

Ala Phe Phe Phe Leu Ala Thr Tyr Gly Asp Gly Glu Pro Thr Asp Asn
                165                 170                 175

Ala Ala Arg Phe Tyr Lys Trp Phe Thr Glu Gly Asn Asp Arg Gly Glu
            180                 185                 190

Trp Leu Lys Asn Leu Lys Tyr Gly Val Phe Gly Leu Gly Asn Arg Gln
        195                 200                 205

Tyr Glu His Phe Asn Lys Val Ala Lys Val Val Asp Asp Ile Leu Val
    210                 215                 220

Glu Gln Gly Ala Gln Arg Leu Val Gln Val Gly Leu Gly Asp Asp Asp
225                 230                 235                 240

Gln Cys Ile Glu Asp Asp Phe Thr Ala Trp Arg Glu Ala Leu Trp Pro
                245                 250                 255

Glu Leu Asp Thr Ile Leu Arg Glu Glu Gly Asp Thr Ala Val Ala Thr
            260                 265                 270

Pro Tyr Thr Ala Ala Val Leu Glu Tyr Arg Val Ser Ile His Asp Ser
        275                 280                 285

Glu Asp Ala Lys Phe Asn Asp Ile Asn Met Ala Asn Gly Asn Gly Tyr
    290                 295                 300

Thr Val Phe Asp Ala Gln His Pro Tyr Lys Ala Asn Val Ala Val Lys
```

```
            305                 310                 315                 320
Arg Glu Leu His Thr Pro Glu Ser Asp Arg Ser Cys Ile His Leu Glu
                    325                 330                 335

Phe Asp Ile Ala Gly Ser Gly Leu Thr Tyr Glu Thr Gly Asp His Val
                    340                 345                 350

Gly Val Leu Cys Asp Asn Leu Ser Glu Thr Val Asp Glu Ala Leu Arg
                    355                 360                 365

Leu Leu Asp Met Ser Pro Asp Thr Tyr Phe Ser Leu His Ala Glu Lys
                    370                 375                 380

Glu Asp Gly Thr Pro Ile Ser Ser Ser Leu Pro Pro Phe Pro Pro
385                 390                 395                 400

Cys Asn Leu Arg Thr Ala Leu Thr Arg Tyr Ala Cys Leu Leu Ser Ser
                    405                 410                 415

Pro Lys Lys Ser Ala Leu Val Ala Leu Ala Ala His Ala Ser Asp Pro
                    420                 425                 430

Thr Glu Ala Glu Arg Leu Lys His Leu Ala Ser Pro Ala Gly Lys Val
                    435                 440                 445

Asp Glu Tyr Ser Lys Trp Val Val Glu Ser Gln Arg Ser Leu Leu Glu
                    450                 455                 460

Val Met Ala Glu Phe Pro Ser Ala Lys Pro Pro Leu Gly Val Phe Phe
465                 470                 475                 480

Ala Gly Val Ala Pro Arg Leu Gln Pro Arg Phe Tyr Ser Ile Ser Ser
                    485                 490                 495

Ser Pro Lys Ile Ala Glu Thr Arg Ile His Val Thr Cys Ala Leu Val
                    500                 505                 510

Tyr Glu Lys Met Pro Thr Gly Arg Ile His Lys Gly Val Cys Ser Thr
                    515                 520                 525

Trp Met Lys Asn Ala Val Pro Tyr Glu Lys Ser Glu Asn Cys Ser Ser
                    530                 535                 540

Ala Pro Ile Phe Val Arg Gln Ser Asn Phe Lys Leu Pro Ser Asp Ser
545                 550                 555                 560

Lys Val Pro Ile Ile Met Ile Gly Pro Gly Thr Gly Leu Ala Pro Phe
                    565                 570                 575

Arg Gly Phe Leu Gln Glu Arg Leu Ala Leu Val Glu Ser Gly Val Glu
                    580                 585                 590

Leu Gly Pro Ser Val Leu Phe Phe Gly Cys Arg Asn Arg Arg Met Asp
                    595                 600                 605

Phe Ile Tyr Glu Glu Glu Leu Gln Arg Phe Val Glu Ser Gly Ala Leu
                    610                 615                 620

Ala Glu Leu Ser Val Ala Phe Ser Arg Glu Gly Pro Thr Lys Glu Tyr
625                 630                 635                 640

Val Gln His Lys Met Met Asp Lys Ala Ser Asp Ile Trp Asn Met Ile
                    645                 650                 655

Ser Gln Gly Ala Tyr Leu Tyr Val Cys Gly Asp Ala Lys Gly Met Ala
                    660                 665                 670

Arg Asp Val His Arg Ser Leu His Thr Ile Ala Gln Glu Gln Gly Ser
                    675                 680                 685

Met Asp Ser Thr Lys Ala Glu Gly Phe Val Lys Asn Leu Gln Thr Ser
                    690                 695                 700

Gly Arg Tyr Leu Arg Asp Val Trp
705                 710

<210> SEQ ID NO 8
```

<211> LENGTH: 641
<212> TYPE: PRT
<213> ORGANISM: Artificial Sequence
<220> FEATURE:
<223> OTHER INFORMATION: AtCPR mutant trAtCPR

<400> SEQUENCE: 8

```
Met Arg Arg Ser Gly Ser Gly Asn Ser Lys Arg Val Glu Pro Leu Lys
1               5                   10                  15

Pro Leu Val Ile Lys Pro Arg Glu Glu Ile Asp Asp Gly Arg Lys
            20                  25                  30

Lys Val Thr Ile Phe Phe Gly Thr Gln Thr Gly Thr Ala Glu Gly Phe
            35                  40                  45

Ala Lys Ala Leu Gly Glu Glu Ala Lys Ala Arg Tyr Glu Lys Thr Arg
50                  55                  60

Phe Lys Ile Val Asp Leu Asp Asp Tyr Ala Ala Asp Asp Glu Tyr
65                  70                  75                  80

Glu Glu Lys Leu Lys Lys Glu Asp Val Ala Phe Phe Leu Ala Thr
                85                  90                  95

Tyr Gly Asp Gly Glu Pro Thr Asp Asn Ala Ala Arg Phe Tyr Lys Trp
            100                 105                 110

Phe Thr Glu Gly Asn Asp Arg Gly Glu Trp Leu Lys Asn Leu Lys Tyr
            115                 120                 125

Gly Val Phe Gly Leu Gly Asn Arg Gln Tyr Glu His Phe Asn Lys Val
130                 135                 140

Ala Lys Val Val Asp Asp Ile Leu Val Glu Gln Gly Ala Gln Arg Leu
145                 150                 155                 160

Val Gln Val Gly Leu Gly Asp Asp Gln Cys Ile Glu Asp Asp Phe
            165                 170                 175

Thr Ala Trp Arg Glu Ala Leu Trp Pro Glu Leu Asp Thr Ile Leu Arg
            180                 185                 190

Glu Glu Gly Asp Thr Ala Val Ala Thr Pro Tyr Thr Ala Ala Val Leu
            195                 200                 205

Glu Tyr Arg Val Ser Ile His Asp Ser Glu Asp Ala Lys Phe Asn Asp
210                 215                 220

Ile Asn Met Ala Asn Gly Asn Gly Tyr Thr Val Phe Asp Ala Gln His
225                 230                 235                 240

Pro Tyr Lys Ala Asn Val Ala Val Lys Arg Glu Leu His Thr Pro Glu
            245                 250                 255

Ser Asp Arg Ser Cys Ile His Leu Glu Phe Asp Ile Ala Gly Ser Gly
            260                 265                 270

Leu Thr Tyr Glu Thr Gly Asp His Val Gly Val Leu Cys Asp Asn Leu
            275                 280                 285

Ser Glu Thr Val Asp Glu Ala Leu Arg Leu Leu Asp Met Ser Pro Asp
            290                 295                 300

Thr Tyr Phe Ser Leu His Ala Glu Lys Glu Asp Gly Thr Pro Ile Ser
305                 310                 315                 320

Ser Ser Leu Pro Pro Pro Phe Pro Pro Cys Asn Leu Arg Thr Ala Leu
            325                 330                 335

Thr Arg Tyr Ala Cys Leu Leu Ser Pro Lys Lys Ser Ala Leu Val
            340                 345                 350

Ala Leu Ala Ala His Ala Ser Asp Pro Thr Glu Ala Glu Arg Leu Lys
            355                 360                 365

His Leu Ala Ser Pro Ala Gly Lys Val Asp Glu Tyr Ser Lys Trp Val
            370                 375                 380
```

Val Glu Ser Gln Arg Ser Leu Leu Glu Val Met Ala Glu Phe Pro Ser
385                 390                 395                 400

Ala Lys Pro Pro Leu Gly Val Phe Phe Ala Gly Val Ala Pro Arg Leu
            405                 410                 415

Gln Pro Arg Phe Tyr Ser Ile Ser Ser Pro Lys Ile Ala Glu Thr
        420                 425                 430

Arg Ile His Val Thr Cys Ala Leu Val Tyr Glu Lys Met Pro Thr Gly
            435                 440                 445

Arg Ile His Lys Gly Val Cys Ser Thr Trp Met Lys Asn Ala Val Pro
        450                 455                 460

Tyr Glu Lys Ser Glu Asn Cys Ser Ser Ala Pro Ile Phe Val Arg Gln
465                 470                 475                 480

Ser Asn Phe Lys Leu Pro Ser Asp Ser Lys Val Pro Ile Ile Met Ile
            485                 490                 495

Gly Pro Gly Thr Gly Leu Ala Pro Phe Arg Gly Phe Leu Gln Glu Arg
        500                 505                 510

Leu Ala Leu Val Glu Ser Gly Val Glu Leu Gly Pro Ser Val Leu Phe
            515                 520                 525

Phe Gly Cys Arg Asn Arg Arg Met Asp Phe Ile Tyr Glu Glu Glu Leu
        530                 535                 540

Gln Arg Phe Val Glu Ser Gly Ala Leu Ala Glu Leu Ser Val Ala Phe
545                 550                 555                 560

Ser Arg Glu Gly Pro Thr Lys Glu Tyr Val Gln His Lys Met Met Asp
            565                 570                 575

Lys Ala Ser Asp Ile Trp Asn Met Ile Ser Gln Gly Ala Tyr Leu Tyr
        580                 585                 590

Val Cys Gly Asp Ala Lys Gly Met Ala Arg Asp Val His Arg Ser Leu
            595                 600                 605

His Thr Ile Ala Gln Glu Gln Gly Ser Met Asp Ser Thr Lys Ala Glu
        610                 615                 620

Gly Phe Val Lys Asn Leu Gln Thr Ser Gly Arg Tyr Leu Arg Asp Val
625                 630                 635                 640

Trp

<210> SEQ ID NO 9
<211> LENGTH: 25
<212> TYPE: DNA
<213> ORGANISM: Artificial Sequence
<220> FEATURE:
<223> OTHER INFORMATION: Primer

<400> SEQUENCE: 9
tataccatgg aactgagcag tgtga                                 25

<210> SEQ ID NO 10
<211> LENGTH: 36
<212> TYPE: DNA
<213> ORGANISM: Artificial Sequence
<220> FEATURE:
<223> OTHER INFORMATION: Primer

<400> SEQUENCE: 10
ctcgaattcg gatccactag tttaatataa agtcgg                     36

<210> SEQ ID NO 11
<211> LENGTH: 43
<212> TYPE: DNA

```
<213> ORGANISM: Artificial Sequence
<220> FEATURE:
<223> OTHER INFORMATION: Primer

<400> SEQUENCE: 11
ctttaagaag gagatatacc atggcgatgc cgaagaaaag ctc                         43

<210> SEQ ID NO 12
<211> LENGTH: 63
<212> TYPE: DNA
<213> ORGANISM: Artificial Sequence
<220> FEATURE:
<223> OTHER INFORMATION: Primer

<400> SEQUENCE: 12
ctttaagaag gagatatacc atggctctgt tattagcagt ttttatgccg aagaaaagct      60
ctt                                                                    63

<210> SEQ ID NO 13
<211> LENGTH: 39
<212> TYPE: DNA
<213> ORGANISM: Artificial Sequence
<220> FEATURE:
<223> OTHER INFORMATION: Primer

<400> SEQUENCE: 13
ctttaagaag gagatatacc atggctaaaa tcgaagaag                             39

<210> SEQ ID NO 14
<211> LENGTH: 35
<212> TYPE: DNA
<213> ORGANISM: Artificial Sequence
<220> FEATURE:
<223> OTHER INFORMATION: Primer

<400> SEQUENCE: 14
ctgaaagacg cgcagactat gccgaagaaa agctc                                 35

<210> SEQ ID NO 15
<211> LENGTH: 35
<212> TYPE: DNA
<213> ORGANISM: Artificial Sequence
<220> FEATURE:
<223> OTHER INFORMATION: Primer

<400> SEQUENCE: 15
gagcttttct tcggcatagt ctgcgcgtct ttcag                                 35

<210> SEQ ID NO 16
<211> LENGTH: 87
<212> TYPE: DNA
<213> ORGANISM: Artificial Sequence
<220> FEATURE:
<223> OTHER INFORMATION: Primer

<400> SEQUENCE: 16
ctttaagaag gagatatacc atggctaaga aaacgagctc taaagggaag ctcccaccag      60
gacctagcat gccgaagaaa agctctt                                          87

<210> SEQ ID NO 17
<211> LENGTH: 44
<212> TYPE: DNA
<213> ORGANISM: Artificial Sequence
<220> FEATURE:
<223> OTHER INFORMATION: Primer
```

```
<400> SEQUENCE: 17
ctttaagaag gagatatacc atggcggact cagaagtcaa tctt            44

<210> SEQ ID NO 18
<211> LENGTH: 36
<212> TYPE: DNA
<213> ORGANISM: Artificial Sequence
<220> FEATURE:
<223> OTHER INFORMATION: Primer

<400> SEQUENCE: 18
gagaacagat tggtggtatg ccgaagaaaa gctctt                     36

<210> SEQ ID NO 19
<211> LENGTH: 36
<212> TYPE: DNA
<213> ORGANISM: Artificial Sequence
<220> FEATURE:
<223> OTHER INFORMATION: Primer

<400> SEQUENCE: 19
aagagctttt cttcggcata ccaccaatct gttctc                     36

<210> SEQ ID NO 20
<211> LENGTH: 27
<212> TYPE: DNA
<213> ORGANISM: Artificial Sequence
<220> FEATURE:
<223> OTHER INFORMATION: Primer

<400> SEQUENCE: 20
tataccatgg gtgactgcgt tgccccg                               27

<210> SEQ ID NO 21
<211> LENGTH: 30
<212> TYPE: DNA
<213> ORGANISM: Artificial Sequence
<220> FEATURE:
<223> OTHER INFORMATION: Primer

<400> SEQUENCE: 21
cgggatcctt acttcggcag gtcgccgctc                            30

<210> SEQ ID NO 22
<211> LENGTH: 29
<212> TYPE: DNA
<213> ORGANISM: Artificial Sequence
<220> FEATURE:
<223> OTHER INFORMATION: Primer

<400> SEQUENCE: 22
cgggatccct tatgcgactc ctgcattag                             29

<210> SEQ ID NO 23
<211> LENGTH: 26
<212> TYPE: DNA
<213> ORGANISM: Artificial Sequence
<220> FEATURE:
<223> OTHER INFORMATION: Primer

<400> SEQUENCE: 23
gcccaagctt ttatgccagc atcttc                                26

<210> SEQ ID NO 24
```

```
<211> LENGTH: 31
<212> TYPE: DNA
<213> ORGANISM: Artificial Sequence
<220> FEATURE:
<223> OTHER INFORMATION: Primer

<400> SEQUENCE: 24
agatatacat atggttacgg tggaagaata c                          31

<210> SEQ ID NO 25
<211> LENGTH: 30
<212> TYPE: DNA
<213> ORGANISM: Artificial Sequence
<220> FEATURE:
<223> OTHER INFORMATION: Primer

<400> SEQUENCE: 25
ccgctcgagt taggtagcca cactatgcag                            30

<210> SEQ ID NO 26
<211> LENGTH: 30
<212> TYPE: DNA
<213> ORGANISM: Artificial Sequence
<220> FEATURE:
<223> OTHER INFORMATION: Primer

<400> SEQUENCE: 26
ccgctcgagc tagaaataat tttgtttaac                            30

<210> SEQ ID NO 27
<211> LENGTH: 28
<212> TYPE: DNA
<213> ORGANISM: Artificial Sequence
<220> FEATURE:
<223> OTHER INFORMATION: Primer

<400> SEQUENCE: 27
gagcctaggt tagttaccga ttttaaag                              28

<210> SEQ ID NO 28
<211> LENGTH: 38
<212> TYPE: DNA
<213> ORGANISM: Artificial Sequence
<220> FEATURE:
<223> OTHER INFORMATION: Primer

<400> SEQUENCE: 28
gaagatgctg gcataaaagc ttcgatcccg cgaaatta                   38

<210> SEQ ID NO 29
<211> LENGTH: 38
<212> TYPE: DNA
<213> ORGANISM: Artificial Sequence
<220> FEATURE:
<223> OTHER INFORMATION: Primer

<400> SEQUENCE: 29
cgacttaagc attatgcggc cgcctacgcc aggttttc                   38
```